US008404453B2

(12) United States Patent
Basilico et al.

(10) Patent No.: US 8,404,453 B2
(45) Date of Patent: Mar. 26, 2013

(54) HIGH AFFINITY BINDING SITE OF HGFR AND METHODS FOR IDENTIFICATION OF ANTAGONISTS THEREOF

(75) Inventors: Cristina Basilico, Pavarolo (IT); Paolo Michieli, Rivalta di Torino (IT); Paolo Carminati, Milan (IT); Paolo Maria Comoglio, Turin (IT)

(73) Assignee: Metheresis Translational Research SA, Lugano (CH)

( * ) Notice: Subject to any disclaimer, the term of this patent is extended or adjusted under 35 U.S.C. 154(b) by 613 days.

(21) Appl. No.: 12/465,307

(22) Filed: May 13, 2009

(65) Prior Publication Data

US 2009/0298079 A1 Dec. 3, 2009

(30) Foreign Application Priority Data

May 14, 2008 (EP) .................................... 08103958

(51) Int. Cl.

| | |
|---|---|
| ***C12Q 1/48*** | (2006.01) |
| ***G01N 33/48*** | (2006.01) |
| ***G01N 33/483*** | (2006.01) |
| ***G01N 33/50*** | (2006.01) |
| *C07K 14/71* | (2006.01) |

(52) U.S. Cl. ............. 435/7.21; 435/4; 435/7.1; 435/7.2; 435/7.23; 435/7.8; 435/15; 435/455; 435/325; 530/395

(58) Field of Classification Search ............... 435/4, 7.1, 435/7.2, 7.21, 7.23, 7.8, 15, 455, 325; 530/395
See application file for complete search history.

(56) References Cited

U.S. PATENT DOCUMENTS 6,207,152 B1 * 3/2001 Schwall et al. ............ 424/130.1

FOREIGN PATENT DOCUMENTS

| | | |
|---|---|---|
| EP | 0 520 158 | 12/1992 |
| EP | 1 243 596 | 9/2002 |
| RU | 2006124743 | 1/2008 |
| WO | WO 2005/058965 | 6/2005 |
| WO | WO 2007/036945 | 4/2007 |
| WO | WO 2007/090807 | 8/2007 |

OTHER PUBLICATIONS

Petrelli, A., et al., Proc. Nat. Acad. Sci., USA, 103(13): 5090-5095, Mar. 28, 2006.*

Eurasian Search Report issued Sep. 14, 2009 in connection with corresponding Eurasian Patent Application No. 200900537.

Gherardi, E. et al, PNAS, vol. 100, No. 21, pp. 12039-12044, Oct. 14, 2003, "Functional map and domain structure of MET, the product of the c-met protooncogene and receptor for hepatocyte growth factor/scatter factor."

Migliore C. et al., "Molecular cancer therapy: can our expectation be MET?" European Journal of Cancer, 44: 641-651, (2008).

Madhusudan S. et al., "Tyrosine kinase inhibitors in cancer therapy", Clinical Biochemistry, 37: 618-635, (2004).

European Search Report dated Sep. 2, 2009—EP Appln. No. 09159644.5.

Michieli et al, "Targeting the tumor and its microenvironment by a dual-function decoy Met receptor", Cancer Cell 6(1):61-73 (2004).

Wang et al, "Potent and selective inhibitors of the Met [hepatocyte growth factor/scatter factor (HGF/SF) receptor] tyrosine kinase block HGF/SF-induced tumor cell growth and invasion", Molecular Cancer Therapeutics 2(11):1085-1092 (2003).

Kaji et al, "Participation of c-*met*in the progression of human gastric cancers: anti-c-*met*oligonucleotides inhibit proliferation or invasiveness of gastric cancer cells", Cancer Gene Therapy 3(6):393-404 (1996).

Kong-Beltran et al, "The Sema domain of Met is necessary for receptor dimerization and activation", Cancer Cell 6(1):75-84 (2004).

Basilico et al, "A High Affinity Hepatocyte Growth Factor-binding Site in the Immunoglobulin-like Region of Met", Journal of Biological Chemistry 283(30):21257-21277 (2008).

* cited by examiner

*Primary Examiner* — Alana Harris Dent
*Assistant Examiner* — Anne Holleran
(74) *Attorney, Agent, or Firm* — Nixon & Vanderhye P.C.

(57) ABSTRACT

Use of a polynucleotide encoding or a polypeptide comprising at least the extracellular IPT-3 and IPT-4 domains of hepatocyte growth factor receptor for the screening and/or development of pharmacologically active agents useful in the treatment of cancer, preferably a cancer with dysregulation of hepatocyte growth factor receptor.

13 Claims, 6 Drawing Sheets

SEQUENCE LISTING

```
<160> NUMBER OF SEQ ID NOS: 21

<210> SEQ ID NO 1
<211> LENGTH: 7425
<212> TYPE: DNA
<213> ORGANISM: artificial
<220> FEATURE:
<223> OTHER INFORMATION: pRRLsin.PPT.CMV.eGPF.Wpre (the eGFP coding
      sequence starts at nucleotide 4756 and finishes at nucleotide
      5745)

<400> SEQUENCE: 1
```

```
caggtggcac ttttcgggga aatgtgcgcg gaacccctat ttgtttattt ttctaaatac     60
attcaaatat gtatccgctc atgagacaat aaccctgata aatgcttcaa taatattgaa    120
aaaggaagag tatgagtatt caacatttcc gtgtcgccct tattcccttt tttgcggcat    180
tttgccttcc tgtttttgct cacccagaaa cgctggtgaa agtaaaagat gctgaagatc    240
agttgggtgc acgagtgggt tacatcgaac tggatctcaa cagcggtaag atccttgaga    300
gttttcgccc cgaagaacgt tttccaatga tgagcacttt taaagttctg ctatgtggcg    360
cggtattatc ccgtattgac gccgggcaag agcaactcgg tcgccgcata cactattctc    420
agaatgactt ggttgagtac tcaccagtca cagaaaagca tcttacggat ggcatgacag    480
taagagaatt atgcagtgct gccataacca tgagtgataa cactgcggcc aacttacttc    540
tgacaacgat cggaggaccg aaggagctaa ccgctttttt gcacaacatg ggggatcatg    600
taactcgcct tgatcgttgg gaaccggagc tgaatgaagc cataccaaac gacgagcgtg    660
acaccacgat gcctgtagca atggcaacaa cgttgcgcaa actattaact ggcgaactac    720
ttactctagc ttcccggcaa caattaatag actggatgga ggcggataaa gttgcaggac    780
cacttctgcg ctcggccctt ccggctggct ggtttattgc tgataaatct ggagccggtg    840
agcgtgggtc tcgcggtatc attgcagcac tggggccaga tggtaagccc tcccgtatcg    900
tagttatcta cacgacgggg agtcaggcaa ctatggatga acgaaataga cagatcgctg    960
agataggtgc ctcactgatt aagcattggt aactgtcaga ccaagtttac tcatatatac   1020
tttagattga tttaaaactt catttttaat ttaaaaggat ctaggtgaag atcctttttg   1080
ataatctcat gaccaaaatc ccttaacgtg agttttcgtt ccactgagcg tcagaccccg   1140
tagaaaagat caaaggatct tcttgagatc cttttttct gcgcgtaatc tgctgcttgc    1200
aaacaaaaaa accaccgcta ccagcggtgg tttgtttgcc ggatcaagag ctaccaactc   1260
tttttccgaa ggtaactggc ttcagcagag cgcagatacc aaatactgtc cttctagtgt   1320
agccgtagtt aggccaccac ttcaagaact ctgtagcacc gcctacatac ctcgctctgc   1380
taatcctgtt accagtggct gctgccagtg gcgataagtc gtgtcttacc gggttggact   1440
caagacgata gttaccggat aaggcgcagc ggtcgggctg aacggggggt tcgtgcacac   1500
agcccagctt ggagcgaacg acctacaccg aactgagata cctacagcgt gagctatgag   1560
aaagcgccac gcttcccgaa gggagaaagg cggacaggta tccggtaagc ggcagggtcg   1620
gaacaggaga gcgcacgagg gagcttccag ggggaaacgc ctggtatctt tatagtcctg   1680
tcgggtttcg ccacctctga cttgagcgtc gatttttgtg atgctcgtca ggggggcgga   1740
gcctatggaa aaacgccagc aacgcggcct ttttacggtt cctggccttt tgctggcctt   1800
ttgctcacat gttctttcct gcgttatccc ctgattctgt ggataaccgt attaccgcct   1860
ttgagtgagc tgataccgct cgccgcagcc gaacgaccga gcgcagcgag tcagtgagcg   1920
aggaagcgga agagcgccca atacgcaaac cgcctctccc cgcgcgttgg ccgattcatt   1980
aatgcagctg gcacgacagg tttcccgact ggaaagcggg cagtgagcgc aacgcaatta   2040
atgtgagtta gctcactcat taggcacccc aggctttaca ctttatgctt ccggctcgta   2100
tgttgtgtgg aattgtgagc ggataacaat ttcacacagg aaacagctat gaccatgatt   2160
acgccaagcg cgcaattaac cctcactaaa gggaacaaaa gctggagctg caagcttaat   2220
gtagtcttat gcaatactct tgtagtcttg caacatggta acgatgagtt agcaacatgc   2280
cttacaagga gagaaaaagc accgtgcatg ccgattggtg gaagtaaggt ggtacgatcg   2340
tgccttatta ggaaggcaac agacgggtct gacatggatt ggacgaacca ctgaattgcc   2400
```

```
gcattgcaga gatattgtat ttaagtgcct agctcgatac aataaacggg tctctctggt    2460

tagaccagat ctgagcctgg gagctctctg gctaactagg gaacccactg cttaagcctc    2520

aataaagctt gccttgagtg cttcaagtag tgtgtgcccg tctgttgtgt gactctggta    2580

actagagatc cctcagaccc ttttagtcag tgtggaaaat ctctagcagt ggcgcccgaa    2640

cagggacctg aaagcgaaag ggaaaccaga gctctctcga cgcaggactc ggcttgctga    2700

agcgcgcacg gcaagaggcg aggggcggcg actggtgagt acgccaaaaa ttttgactag    2760

cggaggctag aaggagagag atgggtgcga gagcgtcagt attaagcggg ggagaattag    2820

atcgcgatgg gaaaaaattc ggttaaggcc agggggaaag aaaaaatata aattaaaaca    2880

tatagtatgg gcaagcaggg agctagaacg attcgcagtt aatcctggcc tgttagaaac    2940

atcagaaggc tgtagacaaa tactgggaca gctacaacca tcccttcaga caggatcaga    3000

agaacttaga tcattatata atacagtagc aaccctctat tgtgtgcatc aaaggataga    3060

gataaaagac accaaggaag ctttagacaa gatagaggaa gagcaaaaca aaagtaagac    3120

caccgcacag caagcggccg ctgatcttca gacctggagg aggagatatg agggacaatt    3180

ggagaagtga attatataaa tataaagtag taaaaattga accattagga gtagcaccca    3240

ccaaggcaaa gagaagagtg gtgcagagag aaaaaagagc agtgggaata ggagctttgt    3300

tccttgggtt cttgggagca gcaggaagca ctatgggcgc agcctcaatg acgctgacgg    3360

tacaggccag acaattattg tctggtatag tgcagcagca gaacaatttg ctgagggcta    3420

ttgaggcgca acagcatctg ttgcaactca cagtctgggg catcaagcag ctccaggcaa    3480

gaatcctggc tgtggaaaga tacctaaagg atcaacagct cctggggatt tggggttgct    3540

ctggaaaact catttgcacc actgctgtgc cttggaatgc tagttggagt aataaatctc    3600

tggaacagat ttggaatcac acgacctgga tggagtggga cagagaaatt aacaattaca    3660

caagcttaat acactcctta attgaagaat cgcaaaacca gcaagaaaag aatgaacaag    3720

aattattgga attagataaa tgggcaagtt tgtggaattg gtttaacata acaaattggc    3780

tgtggtatat aaaattattc ataatgatag taggaggctt ggtaggttta agaatagttt    3840

ttgctgtact ttctatagtg aatagagtta ggcagggata ttcaccatta tcgtttcaga    3900

cccacctccc aaccccgagg ggacccgaca ggcccgaagg aatagaagaa gaaggtggag    3960

agagagacag agacagatcc attcgattag tgaacggatc tcgacggtta acttttaaaa    4020

gaaaaggggg gattgggggg tacagtgcag gggaaagaat agtagacata atagcaacag    4080

acatacaaac taaagaatta caaaaacaaa ttacaaaaat tcaaaatttt atcgataagc    4140

ttgggagttc cgcgttacat aacttacggt aaatggcccg cctggctgac cgcccaacga    4200

cccccgccca ttgacgtcaa taatgacgta tgttcccata gtaacgccaa tagggacttt    4260

ccattgacgt caatgggtgg agtatttacg gtaaactgcc cacttggcag tacatcaagt    4320

gtatcatatg ccaagtacgc cccctattga cgtcaatgac ggtaaatggc ccgcctggca    4380

ttatgcccag tacatgacct tatgggactt tcctacttgg cagtacatct acgtattagt    4440

catcgctatt accatggtga tgcggttttg gcagtacatc aatgggcgtg gatagcggtt    4500

tgactcacgg ggatttccaa gtctccaccc cattgacgtc aatgggagtt tgttttggca    4560

ccaaaatcaa cgggactttc caaaatgtcg taacaactcc gccccattga cgcaaatggg    4620

cggtaggcgt gtacggtggg aggtctatat aagcagagct cgtttagtga accgtcagat    4680

cgcctggaga cgccatccac gctgttttga cctccataga agacaccgac tctagaggat    4740

ccaccggtcg ccaccatggt gagcaagggc gaggagctgt tcaccggggt ggtgcccatc    4800
```

ctggtcgagc tggacggcga cgtaaacggc cacaagttca gcgtgtccgg cgagggcgag 4860
ggcgatgcca cctacggcaa gctgaccctg aagttcatct gcaccaccgg caagctgccc 4920
gtgccctggc ccaccctcgt gaccaccctg acctacggcg tgcagtgctt cagccgctac 4980
cccgaccaca tgaagcagca cgacttcttc aagtccgcca tgcccgaagg ctacgtccag 5040
gagcgcacca tcttcttcaa ggacgacggc aactacaaga cccgcgccga ggtgaagttc 5100
gagggcgaca ccctggtgaa ccgcatcgag ctgaagggca tcgacttcaa ggaggacggc 5160
aacatcctgg ggcacaagct ggagtacaac tacaacagcc acaacgtcta tatcatggcc 5220
gacaagcaga agaacggcat caaggtgaac ttcaagatcc gccacaacat cgaggacggc 5280
agcgtgcagc tcgccgacca ctaccagcag aacaccccca tcggcgacgg ccccgtgctg 5340
ctgcccgaca accactacct gagcacccag tccgccctga gcaaagaccc caacgagaag 5400
cgcgatcaca tggtcctgct ggagttcgtg accgccgccg ggatcactct cggcatggac 5460
gagctgtaca agtaaagcgg ccgcgtcgac aatcaacctc tggattacaa aatttgtgaa 5520
agattgactg gtattcttaa ctatgttgct ccttttacgc tatgtggata cgctgcttta 5580
atgcctttgt atcatgctat tgcttcccgt atggctttca ttttctcctc cttgtataaa 5640
tcctggttgc tgtctcttta tgaggagttg tggcccgttg tcaggcaacg tggcgtggtg 5700
tgcactgtgt ttgctgacgc aacccccact ggttggggca ttgccaccac ctgtcagctc 5760
ctttccggga ctttcgcttt ccccctccct attgccacgg cggaactcat cgccgcctgc 5820
cttgcccgct gctggacagg ggctcggctg ttgggcactg acaattccgt ggtgttgtcg 5880
gggaagctga cgtcctttcc atggctgctc gcctgtgttg ccacctggat tctgcgcggg 5940
acgtccttct gctacgtccc ttcggccctc aatccagcgg accttccttc ccgcggcctg 6000
ctgccggctc tgcggcctct tccgcgtctt cgccttcgcc ctcagacgag tcggatctcc 6060
ctttgggccg cctccccgcc tggaattcga gctcggtacc tttaagacca atgacttaca 6120
aggcagctgt agatcttagc cactttttaa aagaaaaggg gggactggaa gggctaattc 6180
actcccaacg aagacaagat ctgctttttg cttgtactgg gtctctctgg ttagaccaga 6240
tctgagcctg ggagctctct ggctaactag ggaacccact gcttaagcct caataaagct 6300
tgccttgagt gcttcaagta gtgtgtgccc gtctgttgtg tgactctggt aactagagat 6360
ccctcagacc cttttagtca gtgtggaaaa tctctagcag tagtagttca tgtcatctta 6420
ttattcagta tttataactt gcaaagaaat gaatatcaga gagtgagagg aacttgttta 6480
ttgcagctta taatggttac aaataaagca atagcatcac aaatttcaca aataaagcat 6540 tttttcact gcattctagt tgtggtttgt ccaaactcat caatgtatct tatcatgtct 6600
ggctctagct atcccgcccc taactccgcc cagttccgcc cattctccgc cccatggctg 6660 actaatttt tttatttatg cagaggccga ggccgcctcg gcctctgagc tattccagaa 6720
gtagtgagga ggcttttttg gaggcctagg cttttgcgtc gagacgtacc caattcgccc 6780
tatagtgagt cgtattacgc gcgctcactg gccgtcgttt tacaacgtcg tgactgggaa 6840
aaccctggcg ttacccaact taatcgcctt gcagcacatc ccccctttcgc cagctggcgt 6900 aatagcgaag aggcccgcac cgatcgccct tcccaacagt tgcgcagcct gaatggcgaa 6960
tggcgcgacg cgccctgtag cggcgcatta agcgcggcgg gtgtggtggt tacgcgcagc 7020
gtgaccgcta cacttgccag cgccctagcg cccgctcctt tcgctttctt cccttccttt 7080
ctcgccacgt tcgccggctt tccccgtcaa gctctaaatc gggggctccc tttagggttc 7140
cgatttagtg ctttacggca cctcgacccc aaaaaacttg attagggtga tggttcacgt 7200
agtgggccat cgccctgata gacggttttt cgccctttga cgttggagtc cacgttcttt 7260
aatagtggac tcttgttcca aactggaaca acactcaacc ctatctcggt ctattctttt 7320
gatttataag ggattttgcc gatttcggcc tattggttaa aaaatgagct gatttaacaa 7380
aaatttaacg cgaattttaa caaaatatta acgtttacaa tttcc 7425

<210> SEQ ID NO 2
<211> LENGTH: 2886
<212> TYPE: DNA
<213> ORGANISM: artificial
<220> FEATURE:
<223> OTHER INFORMATION: Coding sequence of Decoy Met_FLAGhis

<400> SEQUENCE: 2
atgaaggccc ccgctgtgct tgcacctggc atcctcgtgc tcctgtttac cttggtgcag 60
aggagcaatg gggagtgtaa agaggcacta gcaaagtccg agatgaatgt gaatatgaag 120
tatcagcttc ccaacttcac cgcggaaaca cccatccaga atgtcattct acatgagcat 180
cacattttcc ttggtgccac taactacatt tatgttttaa atgaggaaga ccttcagaag 240
gttgctgagt acaagactgg gcctgtgctg gaacacccag attgtttccc atgtcaggac 300
tgcagcagca aagccaattt atcaggaggt gtttggaaag ataacatcaa catggctcta 360
gttgtcgaca cctactatga tgatcaactc attagctgtg gcagcgtcaa cagagggacc 420
tgccagcgac atgtctttcc ccacaatcat actgctgaca tacagtcgga ggttcactgc 480
atattctccc cacagataga agagcccagc cagtgtcctg actgtgtggt gagcgccctg 540
ggagccaaag tcctttcatc tgtaaaggac cggttcatca acttctttgt aggcaatacc 600
ataaattctt cttatttccc agatcatcca ttgcattcga tatcagtgag aaggctaaag 660
gaaacgaaag atggttttat gtttttgacg gaccagtcct acattgatgt tttacctgag 720
ttcagagatt cttaccccat taagtatgtc catgcctttg aaagcaacaa ttttatttac 780
ttcttgacgg tccaaaggga aactctagat gctcagactt ttcacacaag aataatcagg 840
ttctgttcca taaactctgg attgcattcc tacatggaaa tgcctctgga gtgtattctc 900
acagaaaaga gaaaaaagag atccacaaag aaggaagtgt ttaatatact tcaggctgcg 960
tatgtcagca agcctggggc ccagcttgct agacaaatag gagccagcct gaatgatgac 1020
attcttttcg gggtgttcgc acaaagcaag ccagattctg ccgaaccaat ggatcgatct 1080
gccatgtgtg cattccctat caaatatgtc aacgacttct tcaacaagat cgtcaacaaa 1140
aacaatgtga gatgtctcca gcatttttac ggacccaatc atgagcactg ctttaatagg 1200
acacttctga gaaattcatc aggctgtgaa gcgcgccgtg atgaatatcg aacagagttt 1260
accacagctt tgcagcgcgt tgacttattc atgggtcaat tcagcgaagt cctcttaaca 1320
tctatatcca ccttcattaa aggagacctc accatagcta atcttgggac atcagagggt 1380
cgcttcatgc aggttgtggt ttctcgatca ggaccatcaa cccctcatgt gaattttctc 1440
ctggactccc atccagtgtc tccagaagtg attgtggagc atacattaaa ccaaaatggc 1500
tacacactgg ttatcactgg gaagaagatc acgaagatcc cattgaatgg cttgggctgc 1560
agacatttcc agtcctgcag tcaatgcctc tctgccccac cctttgttca gtgtggctgg 1620
tgccacgaca aatgtgtgcg atcggaggaa tgcctgagcg ggacatggac tcaacagatc 1680
tgtctgcctg caatctacaa ggttttccca aatagtgcac cccttgaagg agggacaagg 1740
ctgaccatat gtggctggga ctttggattt cggaggaata ataaatttga tttaaagaaa 1800
actagagttc tccttggaaa tgagagctgc accttgactt taagtgagag cacgatgaat 1860
acattgaaat gcacagttgg tcctgccatg aataagcatt tcaatatgtc cataattatt 1920
tcaaatggcc acgggacaac acaatacagt acattctcct atgtggatcc tgtaataaca 1980
agtatttcgc cgaaatacgg tcctatggct ggtggcactt tacttacttt aactggaaat 2040
tacctaaaca gtgggaattc tagacacatt tcaattggtg gaaaaacatg tactttaaaa 2100
agtgtgtcaa acagtattct tgaatgttat accccagccc aaaccatttc aactgagttt 2160
gctgttaaat tgaaaattga cttagccaac cgagagacaa gcatcttcag ttaccgtgaa 2220
gatcccattg tctatgaaat tcatccaacc aaatctttta ttagtggtgg gagcacaata 2280
acaggtgttg ggaaaaacct gaattcagtt agtgtcccga gaatggtcat aaatgtgcat 2340
gaagcaggaa ggaactttac agtggcatgt caacatcgct ctaattcaga gataatctgt 2400
tgtaccactc cttccctgca acagctgaat ctgcaactcc ccctgaaaac caaagccttt 2460
ttcatgttag atgggatcct ttccaaatac tttgatctca tttatgtaca taatcctgtg 2520
tttaagcctt ttgaaaagcc agtgatgatc tcaatgggca atgaaaatgt actggaaatt 2580
aagggaaatg atattgaccc tgaagcagtt aaaggtgaag tgttaaaagt tggaaataag 2640
agctgtgaga atatacactt acattctgaa gccgttttat gcacggtccc caatgacctg 2700
ctgaaattga acagcgagct aaatatagag tggaagcaag caatttcttc aaccgtcctt 2760
ggaaaagtaa tagttcaacc agatcagaat ttcacagcta gctctgacta caaggacgac 2820
gatgacaaga gcgattacaa agacgatgat gataagctgc agcatcacca ccatcatcac 2880
cattga 2886

<210> SEQ ID NO 3
<211> LENGTH: 1590
<212> TYPE: DNA
<213> ORGANISM: artificial
<220> FEATURE:
<223> OTHER INFORMATION: Coding sequence of Sema_FLAGhis

<400> SEQUENCE: 3
atgaaggccc ccgctgtgct tgcacctggc atcctcgtgc tcctgtttac cttggtgcag 60
aggagcaatg gggagtgtaa agaggcacta gcaaagtccg agatgaatgt gaatatgaag 120
tatcagcttc ccaacttcac cgcggaaaca cccatccaga atgtcattct acatgagcat 180
cacattttcc ttggtgccac taactacatt tatgttttaa atgaggaaga ccttcagaag 240
gttgctgagt acaagactgg gcctgtgctg gaacacccag attgtttccc atgtcaggac 300
tgcagcagca aagccaattt atcaggaggt gtttggaaag ataacatcaa catggctcta 360
gttgtcgaca cctactatga tgatcaactc attagctgtg gcagcgtcaa cagagggacc 420
tgccagcgac atgtctttcc ccacaatcat actgctgaca tacagtcgga ggttcactgc 480
atattctccc cacagataga agagcccagc cagtgtcctg actgtgtggt gagcgccctg 540
ggagccaaag tcctttcatc tgtaaaggac cggttcatca acttctttgt aggcaatacc 600
ataaattctt cttatttccc agatcatcca ttgcattcga tatcagtgag aaggctaaag 660
gaaacgaaag atggttttat gtttttgacg gaccagtcct acattgatgt tttacctgag 720
ttcagagatt cttaccccat taagtatgtc catgcctttg aaagcaacaa ttttatttac 780
ttcttgacgg tccaaaggga aactctagat gctcagactt ttcacacaag aataatcagg 840
ttctgttcca taaactctgg attgcattcc tacatggaaa tgcctctgga gtgtattctc 900
acagaaaaga gaaaaaagag atccacaaag aaggaagtgt ttaatatact tcaggctgcg 960
tatgtcagca agcctggggc ccagcttgct agacaaatag gagccagcct gaatgatgac 1020

```
attcttttcg gggtgttcgc acaaagcaag ccagattctg ccgaaccaat ggatcgatct   1080

gccatgtgtg cattccctat caaatatgtc aacgacttct tcaacaagat cgtcaacaaa   1140

aacaatgtga gatgtctcca gcatttttac ggacccaatc atgagcactg ctttaatagg   1200

acacttctga gaaattcatc aggctgtgaa gcgcgccgtg atgaatatcg aacagagttt   1260

accacagctt tgcagcgcgt tgacttattc atgggtcaat tcagcgaagt cctcttaaca   1320

tctatatcca ccttcattaa aggagacctc accatagcta atcttgggac atcagagggt   1380

cgcttcatgc aggttgtggt ttctcgatca ggaccatcaa cccctcatgt gaattttctc   1440

ctggactccc atccagtgtc tccagaagtg attgtggagc atacattaaa ccaaaatggc   1500

gctagctctg actacaagga cgacgatgac aagagcgatt acaaagacga tgatgataag   1560

ctgcagcatc accaccatca tcaccattag                                    1590
```

<210> SEQ ID NO 4
<211> LENGTH: 1779
<212> TYPE: DNA
<213> ORGANISM: artificial
<220> FEATURE:
<223> OTHER INFORMATION: Coding sequence of Sema-PSI_FLAGhis

<400> SEQUENCE: 4

```
atgaaggccc ccgctgtgct tgcacctggc atcctcgtgc tcctgtttac cttggtgcag     60

aggagcaatg gggagtgtaa agaggcacta gcaaagtccg agatgaatgt gaatatgaag    120

tatcagcttc ccaacttcac cgcggaaaca cccatccaga atgtcattct acatgagcat    180

cacattttcc ttggtgccac taactacatt tatgttttaa atgaggaaga ccttcagaag    240

gttgctgagt acaagactgg gcctgtgctg gaacacccag attgtttccc atgtcaggac    300

tgcagcagca aagccaattt atcaggaggt gtttggaaag ataacatcaa catggctcta    360

gttgtcgaca cctactatga tgatcaactc attagctgtg gcagcgtcaa cagagggacc    420

tgccagcgac atgtctttcc ccacaatcat actgctgaca tacagtcgga ggttcactgc    480

atattctccc cacagataga agagcccagc cagtgtcctg actgtgtggt gagcgccctg    540

ggagccaaag tcctttcatc tgtaaaggac cggttcatca acttctttgt aggcaatacc    600

ataaattctt cttatttccc agatcatcca ttgcattcga tatcagtgag aaggctaaag    660

gaaacgaaag atggttttat gtttttgacg gaccagtcct acattgatgt tttacctgag    720

ttcagagatt cttaccccat taagtatgtc catgcctttg aaagcaacaa ttttatttac    780

ttcttgacgg tccaaaggga aactctagat gctcagactt ttcacacaag aataatcagg    840

ttctgttcca taaactctgg attgcattcc tacatggaaa tgcctctgga gtgtattctc    900

acagaaaaga gaaaaaagag atccacaaag aaggaagtgt ttaatatact tcaggctgcg    960

tatgtcagca agcctggggc ccagcttgct agacaaatag gagccagcct gaatgatgac   1020

attcttttcg gggtgttcgc acaaagcaag ccagattctg ccgaaccaat ggatcgatct   1080

gccatgtgtg cattccctat caaatatgtc aacgacttct tcaacaagat cgtcaacaaa   1140

aacaatgtga gatgtctcca gcatttttac ggacccaatc atgagcactg ctttaatagg   1200

acacttctga gaaattcatc aggctgtgaa gcgcgccgtg atgaatatcg aacagagttt   1260

accacagctt tgcagcgcgt tgacttattc atgggtcaat tcagcgaagt cctcttaaca   1320

tctatatcca ccttcattaa aggagacctc accatagcta atcttgggac atcagagggt   1380

cgcttcatgc aggttgtggt ttctcgatca ggaccatcaa cccctcatgt gaattttctc   1440

ctggactccc atccagtgtc tccagaagtg attgtggagc atacattaaa ccaaaatggc   1500
```

-continued

```
tacacactgg ttatcactgg gaagaagatc acgaagatcc cattgaatgg cttgggctgc   1560

agacatttcc agtcctgcag tcaatgcctc tctgccccac cctttgttca gtgtggctgg   1620

tgccacgaca aatgtgtgcg atcggaggaa tgcctgagcg ggacatggac tcaacagatc   1680

tgtctgggag ctagctctga ctacaaggac gacgatgaca agagcgatta caaagacgat   1740

gatgataagc tgcagcatca ccaccatcat caccattga                          1779
```

<210> SEQ ID NO 5
<211> LENGTH: 1458
<212> TYPE: DNA
<213> ORGANISM: artificial
<220> FEATURE:
<223> OTHER INFORMATION: Coding sequence of PSI-IPT_FLAGhis

<400> SEQUENCE: 5

```
atgaaggccc ccgctgtgct tgcacctggc atcctcgtgc tcctgtttac cttggtgcag     60

aggagcaatg ggtacacact ggttatcact gggaagaaga tcacgaagat cccattgaat    120

ggcttgggct gcagacattt ccagtcctgc agtcaatgcc tctctgcccc accctttgtt    180

cagtgtggct ggtgccacga caaatgtgtg cgatcggagg aatgcctgag cgggacatgg    240

actcaacaga tctgtctgcc tgcaatctac aaggttttcc caaatagtgc accccttgaa    300

ggagggacaa ggctgaccat atgtggctgg gactttggat ttcggaggaa taataaattt    360

gatttaaaga aaactagagt tctccttgga aatgagagct gcaccttgac tttaagtgag    420

agcacgatga atacattgaa atgcacagtt ggtcctgcca tgaataagca tttcaatatg    480

tccataatta tttcaaatgg ccacgggaca acacaataca gtacattctc ctatgtggat    540

cctgtaataa caagtatttc gccgaaatac ggtcctatgg ctggtggcac tttacttact    600

ttaactggaa attacctaaa cagtgggaat tctagacaca tttcaattgg tggaaaaaca    660

tgtactttaa aaagtgtgtc aaacagtatt cttgaatgtt ataccccagc ccaaaccatt    720

tcaactgagt ttgctgttaa attgaaaatt gacttagcca accgagagac aagcatcttc    780

agttaccgtg aagatcccat tgtctatgaa attcatccaa ccaaatcttt tattagtggt    840

gggagcacaa taacaggtgt tgggaaaaac ctgaattcag ttagtgtccc gagaatggtc    900

ataaatgtgc atgaagcagg aaggaacttt acagtggcat gtcaacatcg ctctaattca    960

gagataatct gttgtaccac tccttccctg caacagctga atctgcaact cccccctgaaa   1020

accaaagcct ttttcatgtt agatgggatc ctttccaaat actttgatct catttatgta   1080

cataatcctg tgtttaagcc ttttgaaaag ccagtgatga tctcaatggg caatgaaaat   1140

gtactggaaa ttaagggaaa tgatattgac cctgaagcag ttaaaggtga agtgttaaaa   1200

gttggaaata agagctgtga gaatatacac ttacattctg aagccgtttt atgcacggtc   1260

cccaatgacc tgctgaaatt gaacagcgag ctaaatatag agtggaagca agcaatttct   1320

tcaaccgtcc ttggaaaagt aatagttcaa ccagatcaga atttcacagc tagctctgac   1380

tacaaggacg acgatgacaa gagcgattac aaagacgatg atgataagct gcagcatcac   1440

caccatcatc accattag                                                  1458
```

<210> SEQ ID NO 6
<211> LENGTH: 1290
<212> TYPE: DNA
<213> ORGANISM: artificial
<220> FEATURE:
<223> OTHER INFORMATION: Coding sequence of IPT_FLAGhis

<400> SEQUENCE: 6
atgaaggccc ccgctgtgct tgcacctggc atcctcgtgc tcctgtttac cttggtgcag 60
aggagcaatg gggagggggg cggtggatcc cctgcaatct acaaggtttt cccaaatagt 120
gcaccccttg aaggagggac aaggctgacc atatgtggct gggactttgg atttcggagg 180
aataataaat ttgatttaaa gaaaactaga gttctccttg gaaatgagag ctgcaccttg 240
actttaagtg agagcacgat gaatacattg aaatgcacag ttggtcctgc catgaataag 300
catttcaata tgtccataat tatttcaaat ggccacggga caacacaata cagtacattc 360
tcctatgtgg atcctgtaat aacaagtatt tcgccgaaat acggtcctat ggctggtggc 420
actttactta ctttaactgg aaattaccta aacagtggga attctagaca catttcaatt 480
ggtggaaaaa catgtacttt aaaaagtgtg tcaaacagta ttcttgaatg ttataccccca 540 gcccaaacca tttcaactga gtttgctgtt aaattgaaaa ttgacttagc caaccgagag 600
acaagcatct tcagttaccg tgaagatccc attgtctatg aaattcatcc aaccaaatct 660
tttattagtg gtgggagcac aataacaggt gttgggaaaa acctgaattc agttagtgtc 720
ccgagaatgg tcataaatgt gcatgaagca ggaaggaact ttacagtggc atgtcaacat 780
cgctctaatt cagagataat ctgttgtacc actccttccc tgcaacagct gaatctgcaa 840 ctcccccctga aaaccaaagc ctttttcatg ttagatggga tcctttccaa atactttgat 900
ctcatttatg tacataatcc tgtgtttaag ccttttgaaa agccagtgat gatctcaatg 960
ggcaatgaaa atgtactgga aattaaggga aatgatattg accctgaagc agttaaaggt 1020
gaagtgttaa aagttggaaa taagagctgt gagaatatac acttacattc tgaagccgtt 1080
ttatgcacgg tccccaatga cctgctgaaa ttgaacagcg agctaaatat agagtggaag 1140
caagcaattt cttcaaccgt ccttggaaaa gtaatagttc aaccagatca gaatttcaca 1200
gctagctctg actacaagga cgacgatgac aagagcgatt acaaagacga tgatgataag 1260
ctgcagcatc accaccatca tcaccattga 1290

<210> SEQ ID NO 7
<211> LENGTH: 1008
<212> TYPE: DNA
<213> ORGANISM: artificial
<220> FEATURE:
<223> OTHER INFORMATION: Coding sequence of IPTdelta1_FLAGhis

<400> SEQUENCE: 7
atgaaggccc ccgctgtgct tgcacctggc atcctcgtgc tcctgtttac cttggtgcag 60
aggagcaatg gggagggggg cggtggatct cctgtaataa caagtatttc gccgaaatac 120
ggtcctatgg ctggtggcac tttacttact ttaactggaa attacctaaa cagtgggaat 180
tctagacaca tttcaattgg tggaaaaaca tgtactttaa aaagtgtgtc aaacagtatt 240
cttgaatgtt ataccccagc ccaaaccatt tcaactgagt ttgctgttaa attgaaaatt 300
gacttagcca accgagagac aagcatcttc agttaccgtg aagatcccat tgtctatgaa 360
attcatccaa ccaaatcttt tattagtggt gggagcacaa taacaggtgt tgggaaaaac 420
ctgaattcag ttagtgtccc gagaatggtc ataaatgtgc atgaagcagg aaggaacttt 480
acagtggcat gtcaacatcg ctctaattca gagataatct gttgtaccac tccttccctg 540
caacagctga atctgcaact cccccctgaaa accaaagcct ttttcatgtt agatgggatc 600
ctttccaaat actttgatct catttatgta cataatcctg tgtttaagcc ttttgaaaag 660
ccagtgatga tctcaatggg caatgaaaat gtactggaaa ttaagggaaa tgatattgac 720
cctgaagcag ttaaaggtga agtgttaaaa gttggaaata agagctgtga gaatatacac 780

```
ttacattctg aagccgtttt atgcacggtc cccaatgacc tgctgaaatt gaacagcgag    840

ctaaatatag agtggaagca agcaatttct tcaaccgtcc ttggaaaagt aatagttcaa    900

ccagatcaga atttcacagc tagctctgac tacaaggacg acgatgacaa gagcgattac    960

aaagacgatg atgataagct gcagcatcac caccatcatc accattga                1008
```

<210> SEQ ID NO 8
<211> LENGTH: 753
<212> TYPE: DNA
<213> ORGANISM: artificial
<220> FEATURE:
<223> OTHER INFORMATION: Coding sequence of IPTdelta1-2_FLAGhis

<400> SEQUENCE: 8

```
atgaaggccc ccgctgtgct tgcacctggc atcctcgtgc tcctgtttac cttggtgcag     60

aggagcaatg gggagggggg cggtggatct cccattgtct atgaaattca tccaaccaaa    120

tcttttatta gtggtgggag cacaataaca ggtgttggga aaaacctgaa ttcagttagt    180

gtcccgagaa tggtcataaa tgtgcatgaa gcaggaagga actttacagt ggcatgtcaa    240

catcgctcta attcagagat aatctgttgt accactcctt ccctgcaaca gctgaatctg    300

caactccccc tgaaaaccaa agccttttc atgttagatg ggatcctttc caaatacttt    360

gatctcattt atgtacataa tcctgtgttt aagccttttg aaaagccagt gatgatctca    420

atgggcaatg aaaatgtact ggaaattaag ggaaatgata ttgaccctga agcagttaaa    480

ggtgaagtgt taaaagttgg aaataagagc tgtgagaata tacacttaca ttctgaagcc    540

gttttatgca cggtccccaa tgacctgctg aaattgaaca gcgagctaaa tatagagtgg    600

aagcaagcaa tttcttcaac cgtccttgga aaagtaatag ttcaaccaga tcagaatttc    660

acagctagct ctgactacaa ggacgacgat gacaagagcg attacaaaga cgatgatgat    720

aagctgcagc atcaccacca tcatcaccat tga                                753
```

<210> SEQ ID NO 9
<211> LENGTH: 471
<212> TYPE: DNA
<213> ORGANISM: artificial
<220> FEATURE:
<223> OTHER INFORMATION: Coding sequence of IPT3_FLAGhis

<400> SEQUENCE: 9

```
atgaaggccc ccgctgtgct tgcacctggc atcctcgtgc tcctgtttac cttggtgcag     60

aggagcaatg gggagggggg cggtggatct cccattgtct atgaaattca tccaaccaaa    120

tcttttatta gtggtgggag cacaataaca ggtgttggga aaaacctgaa ttcagttagt    180

gtcccgagaa tggtcataaa tgtgcatgaa gcaggaagga actttacagt ggcatgtcaa    240

catcgctcta attcagagat aatctgttgt accactcctt ccctgcaaca gctgaatctg    300

caactccccc tgaaaaccaa agccttttc atgttagatg ggatcctttc caaatacttt    360

gatctcattt atgtacataa tgctagctct gactacaagg acgacgatga caagagcgat    420

tacaaagacg atgatgataa gctgcagcat caccaccatc atcaccattg a            471
```

<210> SEQ ID NO 10
<211> LENGTH: 462
<212> TYPE: DNA
<213> ORGANISM: artificial
<220> FEATURE:
<223> OTHER INFORMATION: Coding sequence of IPT4_FLAGhis

<400> SEQUENCE: 10
atgaaggccc ccgctgtgct tgcacctggc atcctcgtgc tcctgtttac cttggtgcag 60
aggagcaatg gggagggggg cggtggatct cctgtgttta agccttttga aaagccagtg 120
atgatctcaa tgggcaatga aaatgtactg gaaattaagg gaaatgatat tgaccctgaa 180
gcagttaaag gtgaagtgtt aaaagttgga aataagagct gtgagaatat acacttacat 240
tctgaagccg ttttatgcac ggtccccaat gacctgctga aattgaacag cgagctaaat 300
atagagtgga agcaagcaat ttcttcaacc gtccttggaa aagtaatagt tcaaccagat 360
cagaatttca cagctagctc tgactacaag gacgacgatg acaagagcga ttacaaagac 420
gatgatgata agctgcagca tcaccaccat catcaccatt ga 462

<210> SEQ ID NO 11
<211> LENGTH: 2040
<212> TYPE: DNA
<213> ORGANISM: artificial
<220> FEATURE:
<223> OTHER INFORMATION: Coding sequence for Met delta 25-741

<400> SEQUENCE: 11
atgaaggccc ccgctgtgct tgcacctggc atcctcgtgc tcctgtttac cttggtgcag 60
aggagcaatg gggagggggg cggtggatct cccattgtct atgaaattca tccaaccaaa 120
tcttttatta gtggtgggag cacaataaca ggtgttggga aaaacctgaa ttcagttagt 180
gtcccgagaa tggtcataaa tgtgcatgaa gcaggaagga actttacagt ggcatgtcaa 240
catcgctcta attcagagat aatctgttgt accactcctt ccctgcaaca gctgaatctg 300
caactccccc tgaaaaccaa agcctttttc atgttagatg ggatcctttc caaatacttt 360
gatctcattt atgtacataa tcctgtgttt aagccttttg aaaagccagt gatgatctca 420
atgggcaatg aaaatgtact ggaaattaag ggaaatgata ttgaccctga agcagttaaa 480
ggtgaagtgt taaaagttgg aaataagagc tgtgagaata tacacttaca ttctgaagcc 540
gttttatgca cggtccccaa tgacctgctg aaattgaaca gcgagctaaa tatagagtgg 600
aagcaagcaa tttcttcaac cgtccttgga aaagtaatag ttcaaccaga tcagaatttc 660
acaggattga ttgctggtgt tgtctcaata tcaacagcac tgttattact acttgggttt 720
ttcctgtggc tgaaaaagag aaagcaaatt aaagatctgg gcagtgaatt agttcgctac 780
gatgcaagag tacacactcc tcatttggat aggcttgtaa gtgcccgaag tgtaagccca 840
actacagaaa tggtttcaaa tgaatctgta gactaccgag ctacttttcc agaagatcag 900
tttcctaatt catctcagaa cggttcatgc cgacaagtgc agtatcctct gacagacatg 960
tcccccatcc taactagtgg ggactctgat atatccagtc cattactgca aaatactgtc 1020
cacattgacc tcagtgctct aaatccagag ctggtccagg cagtgcagca tgtagtgatt 1080
gggcccagta gcctgattgt gcatttcaat gaagtcatag gaagagggca ttttggttgt 1140
gtatatcatg ggactttgtt ggacaatgat ggcaagaaaa ttcactgtgc tgtgaaatcc 1200
ttgaacagaa tcactgacat aggagaagtt tcccaatttc tgaccgaggg aatcatcatg 1260
aaagatttta gtcatcccaa tgtcctctcg ctcctgggaa tctgcctgcg aagtgaaggg 1320
tctccgctgg tggtcctacc atacatgaaa catggagatc ttcgaaattt cattcgaaat 1380
gagactcata atccaactgt aaaagatctt attggctttg gtcttcaagt agccaaaggc 1440
atgaaatatc ttgcaagcaa aaagtttgtc cacagagact tggctgcaag aaactgtatg 1500
ctggatgaaa aattcacagt caaggttgct gattttggtc ttgccagaga catgtatgat 1560
aaagaatact atagtgtaca caacaaaaca ggtgcaaagc tgccagtgaa gtggatggct 1620
ttggaaagtc tgcaaactca aaagtttacc accaagtcag atgtgtggtc ctttggcgtg 1680
ctcctctggg agctgatgac aagaggagcc ccaccttatc ctgatgtaaa cacctttgat 1740
ataactgttt acttgttgca agggagaaga ctcctacaac ccgaatactg cccagacccc 1800
ttatatgaag taatgctaaa atgctggcac cctaaagccg aaatgcgccc atccttttct 1860
gaactggtgt cccggatatc agcaatcttc tctactttca ttggggagca ctatgtccat 1920
gtgaacgcta cttatgtgaa cgtaaaatgt gtcgctccat atccttctct gttgtcatca 1980
gaagataacg ctgatgatga ggtggacaca cgaccagcct ccttctggga gacatcatag 2040

<210> SEQ ID NO 12
<211> LENGTH: 2259
<212> TYPE: DNA
<213> ORGANISM: artificial
<220> FEATURE:
<223> OTHER INFORMATION: Coding sequence for HGF_MYChis

<400> SEQUENCE: 12
atgtgggtga ccaaactcct gccagccctg ctgctgcagc atgtcctcct gcatctcctc 60
ctgctcccca tcgccatccc ctatgcagag ggacaaagga aaagaagaaa tacaattcat 120
gaattcaaaa aatcagcaaa gactaccct a atcaaaatag atccagcact gaagataaaa 180
accaaaaaag tgaatactgc agaccaatgt gctaatagat gtactaggaa taaaggactt 240
ccattcactt gcaaggcttt tgtttttgat aaagcaagaa aacaatgcct ctggttcccc 300
ttcaatagca tgtcaagtgg agtgaaaaaa gaatttggcc atgaatttga cctctatgaa 360
aacaaagact acattagaaa ctgcatcatt ggtaaaggac gcagctacaa gggaacagta 420
tctatcacta agagtggcat caaatgtcag ccctggagtt ccatgatacc acacgaacac 480
agctttttgc cttcgagcta tcggggtaaa gacctacagg aaaactactg tcgaaatcct 540
cgaggggaag aagggggacc ctggtgtttc acaagcaatc cagaggtacg ctacgaagtc 600
tgtgacattc ctcagtgttc agaagttgaa tgcatgacct gcaatgggga gagttatcga 660
ggtctcatgg atcatacaga atcaggcaag atttgtcagc gctgggatca tcagacacca 720
caccggcaca aattcttgcc tgaaagatat cccgacaagg gctttgatga taattattgc 780
cgcaatcccg atggccagcc gaggccatgg tgctatactc ttgaccctca cacccgctgg 840
gagtactgtg caattaaaac atgcgctgac aatactatga atgacactga tgttcctttg 900
gaaacaactg aatgcatcca aggtcaagga gaaggctaca ggggcactgt caataccatt 960
tggaatggaa ttccatgtca gcgttgggat tctcagtatc ctcacgagca tgacatgact 1020
cctgaaaatt tcaagtgcaa ggacctacga gaaaattact gccgaaatcc agatgggtct 1080
gaatcaccct ggtgttttac cactgatcca aacatccgag ttggctactg ctcccaaatt 1140
ccaaactgtg atatgtcaca tggacaagat tgttatcgtg ggaatggcaa aaattatatg 1200
ggcaacttat cccaaacaag atctggacta acatgttcaa tgtgggacaa gaacatggaa 1260
gacttacatc gtcatatctt ctgggaacca gatgcaagta agctgaatga gaattactgc 1320
cgaaatccag atgatgatgc tcatggaccc tggtgctaca cgggaaatcc actcattcct 1380
tgggattatt gccctatttc tcgttgtgaa ggtgatacca cacctacaat agtcaattta 1440
gaccatcccg taatatcttg tgccaaaacg aaacaattgc gagttgtaaa tgggattcca 1500
acacgaacaa acataggatg gatggttagt ttgagataca gaaataaaca tatctgcgga 1560
ggatcattga taaaggagag ttgggttctt actgcacgac agtgtttccc ttctcgagac 1620
ttgaaagatt atgaagcttg gcttggaatt catgatgtcc acggaagagg agatgagaaa 1680

```
tgcaaacagg ttctcaatgt ttcccagctg gtatatggcc ctgaaggatc agatctggtt   1740

ttaatgaagc ttgccaggcc tgctgtcctg gatgattttg ttagtacgat tgatttacct   1800

aattatggat gcacaattcc tgaaaagacc agttgcagtg tttatggctg ggctacact    1860

ggattgatca actatgatgg cctattacga gtggcacatc tctatataat gggaaatgag   1920

aaatgcagcc agcatcatcg agggaaggtg actctgaatg agtctgaaat atgtgctggg   1980

gctgaaaaga ttggatcagg accatgtgag gggggattatg gtggcccact tgtttgtgag  2040

caacataaaa tgagaatggt tcttggtgtc attgttcctg gtcgtggatg tgccattcca   2100

aatcgtcctg gtatttttgt ccgagtagca tattatgcaa aatggataca caaaattatt   2160

ttaacatata aggtaccaca gtcagctagc gaacaaaaac tcatctcaga agaggatctg   2220

aatggagggc tcgagcatca ccaccatcac catcattga                          2259
```

<210> SEQ ID NO 13
<211> LENGTH: 1494
<212> TYPE: DNA
<213> ORGANISM: artificial
<220> FEATURE:
<223> OTHER INFORMATION: Coding sequence of HGF-alfa_MYChis

<400> SEQUENCE: 13

```
atgtgggtga ccaaactcct gccagccctg ctgctgcagc atgtcctcct gcatctcctc     60

ctgctcccca tcgccatccc ctatgcagag ggacaaagga aaagaagaaa tacaattcat    120

gaattcaaaa aatcagcaaa gactacccta atcaaaatag atccagcact gaagataaaa    180

accaaaaaag tgaatactgc agaccaatgt gctaatagat gtactaggaa taaaggactt    240

ccattcactt gcaaggcttt tgtttttgat aaagcaagaa aacaatgcct ctggttcccc    300

ttcaatagca tgtcaagtgg agtgaaaaaa gaatttggcc atgaatttga cctctatgaa    360

aacaaagact acattagaaa ctgcatcatt ggtaaaggac gcagctacaa gggaacagta    420

tctatcacta agagtggcat caaatgtcag ccctggagtt ccatgatacc acacgaacac    480

agctttttgc cttcgagcta tcggggtaaa gacctacagg aaaactactg tcgaaatcct    540

cgaggggaag aagggggacc ctggtgtttc acaagcaatc cagaggtacg ctacgaagtc    600

tgtgacattc ctcagtgttc agaagttgaa tgcatgacct gcaatgggga gagttatcga    660

ggtctcatgg atcatacaga atcaggcaag atttgtcagc gctgggatca tcagacacca    720

caccggcaca aattcttgcc tgaaagatat cccgacaagg gctttgatga taattattgc    780

cgcaatcccg atggccagcc gaggccatgg tgctatactc ttgaccctca cacccgctgg    840

gagtactgtg caattaaaac atgcgctgac aatactatga atgacactga tgttcctttg    900

gaaacaactg aatgcatcca aggtcaagga gaaggctaca ggggcactgt caataccatt    960

tggaatggaa ttccatgtca gcgttgggat tctcagtatc ctcacgagca tgacatgact   1020

cctgaaaatt tcaagtgcaa ggacctacga gaaaattact gccgaaatcc agatgggtct   1080

gaatcaccct ggtgttttac cactgatcca aacatccgag ttggctactg ctcccaaatt   1140

ccaaactgtg atatgtcaca tggacaagat tgttatcgtg ggaatggcaa aaattatatg   1200

ggcaacttat cccaaacaag atctggacta acatgttcaa tgtgggacaa gaacatggaa   1260

gacttacatc gtcatatctt ctgggaacca gatgcaagta agctgaatga gaattactgc   1320

cgaaatccag atgatgacgc tcatggaccc tggtgctaca cgggaaatcc actcattcct   1380

tgggattatt gccctatttc tcgttgtgaa ggtgataccg ctagcgaaca aaaactcatc   1440

tcagaagagg atctgaatgg agggctcgag catcaccacc atcaccatca ttga         1494
```

<210> SEQ ID NO 14
<211> LENGTH: 705
<212> TYPE: DNA
<213> ORGANISM: artificial
<220> FEATURE:
<223> OTHER INFORMATION: Coding sequence of HGF NK1_MYChis

<400> SEQUENCE: 14
atgtgggtga ccaaactcct gccagccctg ctgctgcagc atgtcctcct gcatctcctc 60
ctgctcccca tcgccatccc ctatgcagag ggacaaagga aaagaagaaa tacaattcat 120
gaattcaaaa aatcagcaaa gactacccta atcaaaatag atccagcact gaagataaaa 180
accaaaaaag tgaatactgc agaccaatgt gctaatagat gtactaggaa taaaggactt 240
ccattcactt gcaaggcttt tgtttttgat aaagcaagaa aacaatgcct ctggttcccc 300
ttcaatagca tgtcaagtgg agtgaaaaaa gaatttggcc atgaatttga cctctatgaa 360
aacaaagact acattagaaa ctgcatcatt ggtaaaggac gcagctacaa gggaacagta 420
tctatcacta agagtggcat caaatgtcag ccctggagtt ccatgatacc acacgaacac 480
agctttttgc cttcgagcta tcggggtaaa gacctacagg aaaactactg tcgaaatcct 540
cgaggggaag aagggggacc ctggtgtttc acaagcaatc cagaggtacg ctacgaagtc 600
tgtgacattc ctcagtgttc agaagttgaa gctagcgaac aaaaactcat ctcagaagag 660
gatctgaatg gagggctcga gcatcaccac catcaccatc attga 705

<210> SEQ ID NO 15
<211> LENGTH: 903
<212> TYPE: DNA
<213> ORGANISM: artificial
<220> FEATURE:
<223> OTHER INFORMATION: Coding sequence of HGF-beta_MYChis

<400> SEQUENCE: 15
atgtgggtga ccaaactcct gccagccctg ctgctgcagc atgtcctcct gcatctcctc 60
ctgctcccca tcgccatccc ctatgcagag ggacaaagga aaagaagaaa tacaattcat 120
gaattcgttg taaatgggat tccaacacga acaaacatag gatggatggt tagtttgaga 180
tacagaaata aacatatctg cggaggatca ttgataaagg agagttgggt tcttactgca 240
cgacagtgtt tcccttctcg agacttgaaa gattatgaag cttggcttgg aattcatgat 300
gtccacggaa gaggagatga gaaatgcaaa caggttctca atgtttccca gctggtatat 360
ggccctgaag gatcagatct ggttttaatg aagcttgcca ggcctgctgt cctggatgat 420
tttgttagta cgattgattt acctaattat ggagccacaa ttcctgaaaa gaccagttgc 480
agtgtttatg gctggggcta cactggattg atcaactatg atggcctatt acgagtggca 540
catctctata taatgggaaa tgagaaatgc agccagcatc atcgagggaa ggtgactctg 600
aatgagtctg aaatatgtgc tggggctgaa aagattggat caggaccatg tgagggggat 660
tatggtggcc cacttgtttg tgagcaacat aaaatgagaa tggttcttgg tgtcattgtt 720
cctggtcgtg gatgtgccat tccaaatcgt cctggtattt ttgtccgagt agcatattat 780
gcaaaatgga tacacaaaat tattttaaca tataaggtac cacagtcagc tagcgaacaa 840
aaactcatct cagaagagga tctgaatgga gggctcgagc atcaccacca tcaccatcat 900
tga 903

<210> SEQ ID NO 16
<211> LENGTH: 2259

<212> TYPE: DNA
<213> ORGANISM: artificial
<220> FEATURE:
<223> OTHER INFORMATION: Coding sequence of Uncleavable HGF_MYChis

<400> SEQUENCE: 16
atgtgggtga ccaaactcct gccagccctg ctgctgcagc atgtcctcct gcatctcctc 60
ctgctcccca tcgccatccc ctatgcagag ggacaaagga aaagaagaaa tacaattcat 120
gaattcaaaa aatcagcaaa gactacccta atcaaaatag atccagcact gaagataaaa 180
accaaaaaag tgaatactgc agaccaatgt gctaatagat gtactaggaa taaaggactt 240
ccattcactt gcaaggcttt tgtttttgat aaagcaagaa aacaatgcct ctggttcccc 300
ttcaatagca tgtcaagtgg agtgaaaaaa gaatttggcc atgaatttga cctctatgaa 360
aacaaagact acattagaaa ctgcatcatt ggtaaaggac gcagctacaa gggaacagta 420
tctatcacta agagtggcat caaatgtcag ccctggagtt ccatgatacc acacgaacac 480
agctttttgc cttcgagcta tcggggtaaa gacctacagg aaaactactg tcgaaatcct 540
cgaggggaag aagggggacc ctggtgtttc acaagcaatc cagaggtacg ctacgaagtc 600
tgtgacattc ctcagtgttc agaagttgaa tgcatgacct gcaatgggga gagttatcga 660
ggtctcatgg atcatacaga atcaggcaag atttgtcagc gctgggatca tcagacacca 720
caccggcaca aattcttgcc tgaaagatat cccgacaagg gctttgatga taattattgc 780
cgcaatcccg atggccagcc gaggccatgg tgctatactc ttgaccctca cacccgctgg 840
gagtactgtg caattaaaac atgcgctgac aatactatga atgacactga tgttcctttg 900
gaaacaactg aatgcatcca aggtcaagga gaaggctaca ggggcactgt caataccatt 960
tggaatggaa ttccatgtca gcgttgggat tctcagtatc ctcacgagca tgacatgact 1020
cctgaaaatt tcaagtgcaa ggacctacga gaaaattact gccgaaatcc agatgggtct 1080
gaatcaccct ggtgttttac cactgatcca aacatccgag ttggctactg ctcccaaatt 1140
ccaaactgtg atatgtcaca tggacaagat tgttatcgtg ggaatggcaa aaattatatg 1200
ggcaacttat cccaaacaag atctggacta acatgttcaa tgtgggacaa gaacatggaa 1260
gacttacatc gtcatatctt ctgggaacca gatgcaagta agctgaatga gaattactgc 1320
cgaaatccag atgatgatgc tcatggaccc tggtgctaca cgggaaatcc actcattcct 1380
tgggattatt gccctatttc tcgttgtgaa ggtgatacca cacctacaat agtcaattta 1440
gaccatcccg taatatcttg tgccaaaacg aaacaactgc aggttgtaaa tgggattcca 1500
acacgaacaa acataggatg gatggttagt ttgagataca gaaataaaca tatctgcgga 1560
ggatcattga taaaggagag ttgggttctt actgcacgac agtgtttccc ttctcgagac 1620
ttgaaagatt atgaagcttg gcttggaatt catgatgtcc acggaagagg agatgagaaa 1680
tgcaaacagg ttctcaatgt ttcccagctg gtatatggcc ctgaaggatc agatctggtt 1740
ttaatgaagc ttgccaggcc tgctgtcctg gatgattttg ttagtacgat tgatttacct 1800
aattatggat gcacaattcc tgaaaagacc agttgcagtg tttatggctg gggctacact 1860
ggattgatca actatgatgg cctattacga gtggcacatc tctatataat gggaaatgag 1920
aaatgcagcc agcatcatcg agggaaggtg actctgaatg agtctgaaat atgtgctggg 1980
gctgaaaaga ttggatcagg accatgtgag ggggattatg gtggcccact tgtttgtgag 2040
caacataaaa tgagaatggt tcttggtgtc attgttcctg gtcgtggatg tgccattcca 2100
aatcgtcctg gtatttttgt ccgagtagca tattatgcaa aatggataca caaaattatt 2160
ttaacatata aggtaccaca gtcagctagc gaacaaaaac tcatctcaga agaggatctg 2220

-continued aatggagggc tcgagcatca ccaccatcac catcattga 2259

<210> SEQ ID NO 17
<211> LENGTH: 1197
<212> TYPE: DNA
<213> ORGANISM: artificial
<220> FEATURE:
<223> OTHER INFORMATION: Coding sequence of NK1-NK1_his

<400> SEQUENCE: 17
atgtgggtga ccaaactcct gccagccctg ctgctgcagc atgtcctcct gcatctcctc 60
ctgctcccca tcgccatccc ctatgcagag ggacaaagga aaagaagaaa tacaattcat 120
gaattcaaaa aatcagcaaa gactacccta atcaaaatag atccagcact gaagataaaa 180
accaaaaaag tgaatactgc agaccaatgt gctaatagat gtactaggaa taaaggactt 240
ccattcactt gcaaggcttt tgtttttgat aaagcaagaa aacaatgcct ctggttcccc 300
ttcaatagca tgtcaagtgg agtgaaaaaa gaatttggcc atgaatttga cctctatgaa 360
aacaaagact acattagaaa ctgcatcatt ggtaaaggac gcagctacaa gggaacagta 420
tctatcacta agagtggcat caaatgtcag ccctggagtt ccatgatacc acacgaacac 480
agctttttgc cttcgagcta tcggggtaaa gacctacagg aaaactactg tcgaaatcct 540
cgaggggaag aagggggacc ctggtgtttc acaagcaatc cagaggtacg ctacgaagtc 600
tgtgacattc ctcagtgttc agaagttgaa gctagcgaat tcaaaaaatc agcaaagact 660
accctaatca aaatagatcc agcactgaag ataaaaacca aaaaagtgaa tactgcagac 720
caatgtgcta atagatgtac taggaataaa ggacttccat tcacttgcaa ggcttttgtt 780
tttgataaag caagaaaaca atgcctctgg ttccccttca atagcatgtc aagtggagtg 840
aaaaaagaat ttggccatga atttgacctc tatgaaaaca aagactacat tagaaactgc 900
atcattggta aaggacgcag ctacaaggga acagtatcta tcactaagag tggcatcaaa 960
tgtcagccct ggagttccat gataccacac gaacacagct ttttgccttc gagctatcgg 1020
ggtaaagacc tacaggaaaa ctactgtcga aatcctcgag gggaagaagg gggaccctgg 1080
tgtttcacaa gcaatccaga ggtacgctac gaagtctgtg acattcctca gtgttcagaa 1140
gttgaagcta gtgggggtgg tagtggagga gggcatcacc atcatcacca tcactga 1197

<210> SEQ ID NO 18
<211> LENGTH: 1218
<212> TYPE: DNA
<213> ORGANISM: artificial
<220> FEATURE:
<223> OTHER INFORMATION: Coding sequence of hAS_MYC

<400> SEQUENCE: 18
atggaacata aggaagtggt tcttctactt cttttatttc tgaaatcagg tcaaggagtg 60
tatctctcag agtgcaagac tgggaatgga aagaactaca gagggacgat gtccaaaaca 120
aaaaatggca tcacctgtca aaaatggagt tccacttctc cccacagacc tagattctca 180
cctgctacac acccctcaga gggactggag gagaactact gcaggaatcc agacaacgat 240
ccgcaggggc cctggtgcta tactactgat ccagaaaaga gatatgacta ctgcgacatt 300
cttgagtgtg aagaggaatg tatgcattgc agtggagaaa actatgacgg caaaatttcc 360
aagaccatgt ctggactgga atgccaggcc tgggactctc agagcccaca cgctcatgga 420
tacattcctt ccaaatttcc aaacaagaac ctgaagaaga attactgtcg taaccccgat 480
agggagctgc ggccttggtg tttcaccacc gaccccaaca agcgctggga actttgcgac 540

-continued

```
atcccccgct gcacaacacc tccaccatct tctggtccca cctaccagtg tctgaaggga    600

acaggtgaaa actatcgcgg gaatgtggct gttaccgttt ccgggcacac ctgtcagcac    660

tggagtgcac agacccctca cacacataac aggacaccag aaaacttccc ctgcaaaaat    720

ttggatgaaa actactgccg caatcctgac ggaaaaaggg ccccatggtg ccatacaacc    780

aacagccaag tgcggtggga gtactgtaag ataccgtcct gtgactcctc cccagtatcc    840

acggaacaat tggctcccac agcaccacct gagctaaccc ctgtggtcca ggactgctac    900

catggtgatg gacagagcta ccgaggcaca tcctccacca ccaccacagg aaagaagtgt    960

cagtcttggt catctatgac accacaccgg caccagaaga ccccagaaaa ctacccaaat   1020

gctggcctga caatgaacta ctgcaggaat ccagatgccg ataaaggccc ctggtgtttt   1080

accacagacc ccagcgtcag gtgggagtac tgcaacctga aaaaatgctc aggaacagaa   1140

gcggctagcg aacaaaaact catctcagaa gaggatctga atggagggct cgagcatcac   1200

caccatcacc atcattga                                                 1218


<210> SEQ ID NO 19
<211> LENGTH: 9
<212> TYPE: PRT
<213> ORGANISM: artificial
<220> FEATURE:
<223> OTHER INFORMATION: Flag at the C terminus

<400> SEQUENCE: 19

Ser Asp Tyr Lys Asp Asp Asp Asp Lys
1               5


<210> SEQ ID NO 20
<211> LENGTH: 11
<212> TYPE: PRT
<213> ORGANISM: artificial
<220> FEATURE:
<223> OTHER INFORMATION: Single Myc at the C terminus

<400> SEQUENCE: 20

Glu Gln Lys Leu Ile Ser Glu Glu Asp Leu Asn
1               5                   10


<210> SEQ ID NO 21
<211> LENGTH: 7
<212> TYPE: PRT
<213> ORGANISM: artificial
<220> FEATURE:
<223> OTHER INFORMATION: poly-histidine tag

<400> SEQUENCE: 21

His His His His His His His
1               5
```

HIGH AFFINITY BINDING SITE OF HGFR AND METHODS FOR IDENTIFICATION OF ANTAGONISTS THEREOF

This application claims priority to European Application No. 08103958.8, filed 14 May 2008, the entire contents of which is hereby incorporated by reference.

TECHNICAL FIELD OF THE INVENTION

The present invention relates to the area of the hepatocyte growth factor receptor (HGFR) protein. More specifically, the present invention relates to the identification of the high affinity binding site of HGFR for its ligand, the hepatocyte growth factor (HGF), and methods for the identification of antagonists of HGFR targeting the high affinity binding site of HGFR.

BACKGROUND OF THE INVENTION

The hepatocyte growth factor receptor (also known as Met) is a tyrosine kinase and is the product of the c-met proto-oncogene. It consists of a 50 kDa α-subunit and of a 145 kDa β-subunit, which are linked by a disulfide bond, the α-subunit being completely extracellular, while the β-subunit includes (from N- to C-terminus) an extracellular region, a transmembrane domain and a cytoplasmic tyrosine kinase domain. The mature α/β hetero-dimeric receptor is generated by proteolytic processing and terminal glycosilation from a 170 kDa single-chain precursor.

HGF, also known as Scatter Factor, is a heparin-binding glycoprotein with a broad spectrum of biological activities including cell proliferation, motility, survival and morphogenesis. It is synthesized and secreted as an inactive single chain precursor (pro-HGF) that is stored into the extracellular matrix due to its high affinity for proteoglycans. Pro-HGF undergoes proteolytic cleavage at residues R494-V495 to give rise to the biologically active form, a disulfide-linked α/β hetero-dimer, where the α-chain consists of an N-terminal domain followed by four kringle domains and the β-chain shares structural homology with the chymotrypsin family of serine proteases. The β-chain, however, lacks proteolytic activity since two of the three critical residues that form the catalytic triad typical of serine proteases are not conserved in HGF. Despite its inability to signal, pro-HGF binds to Met at high affinity and displaces active HGF.

Recently, a number of structure-function studies have shed some light onto the interactions between the extracellular portion of Met and HGF.

The Met extracellular region has a modular structure, which encompasses three functional domains: the Sema domain (present also in Semaphorins and plexins) which spans the first 500 residues at the N-terminus of the protein and has a seven-bladed β-propeller structure, the PST domain (also found in Plexins, Semaphorins and Integrins) which covers about 50 residues and contains four conserved disulfide bonds, and additional 400 residues which link the PSI domain to the trans-membrane helix and are occupied by four IPT domains (Immunoglobulin-related domains present in Plexins and Transcription factors).

HGF is a bivalent ligand, containing a high affinity binding site for Met in the α-chain and a low affinity binding site in the β-chain. Cooperation between the α- and the β-chain is required for the biological activity of HGF; while the α-chain, and more precisely the N-domain and the first kringle, is sufficient for Met binding, the β-chain is necessary for Met activation.

Resolution of the crystal structure of the SEMA and PSI domains of Met in complex with the β-chain of HGF (see i.a. WO-A-2005/108424) revealed that the low affinity binding site for HGF is located in blades 2-3 of the β-propeller, and that the portion of HGF-β that binds to Met is the same region that serine proteases use to bind to their substrates or inhibitors. Importantly, determination of HGF β-chain crystal structure at 2.53 Å resolution and specific mutagenesis analysis unveiled that the residues involved in Met binding in the activation pocket of HGF β-chain get exposed only following proteolytic conversion of pro-HGF, thus explaining why pro-HGF binds to Met at high affinity without activating it. While the low affinity interaction between the β-chain of HGF and the Sema domain of Met is well characterized both structurally and functionally, at the moment it is not clear what region of Met binds to the α-chain of HGF at high affinity. Thus, the main mechanism by which HGF activates Met still remains poorly understood. This is somehow surprising when considering the great biological and therapeutic importance of this pathway.

HGF-Met signaling is essential during embryogenesis and in tissue regeneration in the adult life. Importantly, deregulated HGF Met signaling plays a key role in tumorigenesis and metastasis. Inappropriate Met activation by different mechanisms including autocrine HGF stimulation, receptor overexpression, gene amplification and point mutation is described in a wide variety of human malignancies and correlates with poor prognosis. These findings resulted in a growing interest in the HGF-Met pathway as a target for cancer therapy, leading to the development of a variety of Met/HGF inhibitors. These include small molecule compounds targeting Met kinase activity, neutralizing anti Met or anti-HGF antibodies, decoy receptors and HGF-derived factors. Nevertheless, whether such molecules target the high affinity binding site for HGF and which is the exact molecular mechanism at the basis of HGF binding to Met at high affinity, remains still unknown. This may prevent from isolating more selective therapeutic agents, with increased sensitivity and fewer side effects. The exact knowledge of the Met high affinity binding site for HGF will certainly help to design highly specific antagonists of Met.

SUMMARY OF THE INVENTION

The need is therefore felt for improved solutions enabling the identification of Met antagonists with increased sensitivity and fewer side effects for the development of more effective therapeutic strategies for the treatment of cancers.

The object of this disclosure is providing such improved solutions.

According to the present invention such objects are achieved thanks to the solution having the characteristics referred to specifically in the ensuing claims. The claims form integral part of the technical teaching herein provided in relation to the present invention.

Thus, object of the present disclosure is the identification of the HGF high affinity binding site to the hepatocyte growth factor receptor (HGFR), i.e. the extracellular IPT-3 and IPT-4 domains of HGFR. A further object of the present invention is to provide means for the identification of antagonists of HGFR targeting the high affinity biding site of HGFR for HGF for the development of new therapeutic strategies for the treatment of cancers.

In an embodiment, the present invention provides for the use of a polypeptide comprising, or a polynucleotide encoding at least the extracellular IPT-3 and IPT-4 domains of hepatocyte growth factor receptor for the screening and/or development of pharmacologically active agents useful in the treatment of cancer, in particular a cancer with dysregulation of hepatocyte growth factor receptor activity.

In an embodiment, the pharmacologically active agent is a hepatocyte growth factor receptor inhibitor and/or antagonist and can be selected among small molecule inhibitors, aptamers, antisense nucleotides, RNA-based inhibitors, siRNAs, antibodies, peptides, dominant negative factors.

In a further embodiment, the present invention concerns a method to detect the ability of a test agent to act as an antagonist/inhibitor of hepatocyte growth factor receptor useful in the treatment of cancer, preferably a cancer with dysregulation of hepatocyte growth factor receptor activity, comprising the steps of:

(a) putting in contact a test agent with at least the extracellular IPT-3 and IPT-4 domains of hepatocyte growth factor receptor, or cells expressing at least the extracellular IPT-3 and IPT-4 domains of hepatocyte growth factor receptor, (b) measuring hepatocyte growth factor receptor activity, function, stability and/or expression, and (c) selecting the agent that reduces hepatocyte growth factor receptor activity, function, stability and/or expression.

In a still further embodiment, the present invention concerns the use of the extracellular IPT-3 and IPT-4 domains of hepatocyte growth factor receptor as a medicament for treating cancer.

BRIEF DESCRIPTION OF THE DRAWINGS

(FIG. 1A) Schematic representation of the engineered proteins used in this study. Left panel: engineered receptors. W.T. MET, wild-type Met; EXTRA, extracellular portion; INTRA, intracellular portion; SP, signal peptide; SEMA, semaphorin homology domain; PSI, plexin-semaphorin-integrin homology domain; IPT 1-4, immunoglobulin-plexin-transcription factor homology domain 1-4; TM, trans-membrane domain; JM, juxta-membrane domain; KD, kinase domain; CT, C-terminal tail; E, FLAG or MYC epitope; H, poly-histidine tag. The red triangle indicates the proteolytic cleavage site between the α- and β-chain. Right panel: engineered ligands. W.T. HGF, wild-type HGF; ND, N-domain; K 1-4, kringle 1-4; PLD, protease-like domain; UNCL. HGF, Uncleavable HGF. The asterisk indicates the R494Q amino acid substitution in the proteolytic site. (FIG. 1B) Coomassie staining of affinity-purified receptors and ligands. Each protein group (Sema, Sema-PSI, Decoy Met; PSI-IPT, IPT; HGF-α, Uncleavable HGF, HGF; HGF NK1, HGF-β) has been resolved by SDS-PAGE in non-reducing conditions and is quantified against a standard curve of bovine serum albumin (BSA). MW, molecular weight marker; kDa, kilo-Dalton.

(FIG. 2A) Binding of Met sub-domains to active HGF. Engineered receptors were immobilized in solid phase and exposed to increasing concentrations of active HGF in liquid phase. Binding was revealed using anti-HGF antibodies. Non-specific binding was measured by using BSA instead of purified receptors in solid phase. (FIGS. 2B-2D) Binding of Decoy Met, Sema-PSI, and IPT to different forms of HGF. Engineered receptors were immobilized in solid phase and exposed to increasing concentrations of MYC-tagged active HGF, pro-HGF, HGF-α or HGF NK1 in liquid phase. Binding was revealed using anti-MYC antibodies. Non-specific binding was measured by using MYC-tagged angiostatin (AS) in liquid phase.

(FIG. 3A) Schematic representation of deleted IPT variants. Color code and legend as in FIG. 1A. (FIG. 3B) ELISA analysis of interactions between IPT variants and HGF-α. Engineered IPTs were immobilized in solid phase and exposed to increasing concentrations of HGF-α in liquid phase. Binding was revealed using anti-HGF antibodies.

(FIG. 4A) Schematic representation of the deleted MetΔ25-741 receptor. Color code and legend as in F*igure* 1A. (FIG. 4B) Surface biotinylation analysis. Cellular proteins were immuno-precipitated (IP) using antibodies directed against the C-terminal portion of Met and analyzed by Western blotting (WB) using horseradish peroxidase-conjugated streptavidin (SA). The same blots were re-probed with anti-Met antibodies. W.T., wild-type; A549, A549 human lung carcinoma cells; MDA, MDA-MB-435 human melanoma cells; TOV, TOV-112D human ovary carcinoma cells; Empty V., empty vector. The p170 band corresponds to unprocessed Met; p145 is the mature form of the receptor. (FIG. 4C) Chemical cross-linking analysis. TOV-112D cells expressing $Met_{\Delta 25\text{-}741}$ (Met Δ25-741) and wild-type TOV-112D cells (W.T. TOV) were incubated with HGF and then subjected to chemical cross-linking. Cell lysates were immuno-precipitated using anti-Met antibodies and analyzed by Western blotting using anti-HGF antibodies. Arrow indicates HGF-$Met_{\Delta 25\text{-}741}$ complexes. (FIG. 4D) Met phosphorylation analysis. TOV-112D cells expressing $Met_{\Delta 25\text{-}741}$ were stimulated with 1% FBS as a negative control and with equal amounts of HGF, pro-HGF, HGF NK1 or NK1-NK1. Receptor phosphorylation was determined by immuno-precipitation with anti-Met antibodies and Western blotting with anti-phosphotyrosine (anti-pTyr) antibodies. The same blots were re-probed using anti-Met antibodies. Arrows indicate bands corresponding to $Met_{\Delta 25\text{-}741}$ or immunoglobulins (Ig). (FIG. 4E) Schematic representation of NK1-NK1. From N- to C-terminus: SP, signal peptide; ND, N-domain; K1, kringle 1; H, poly-histidine tag.

(FIG. 5A) Lentiviral vector transduced MDA-MB-435 cells were stimulated with recombinant HGF and Met phosphorylation was determined by immuno-blotting using anti-phosphotyrosine antibodies (upper panel). The same blot was re-probed using anti-Met antibodies (lower panel). Empty V., Empty Vector. (FIG. 5B) Branching morphogenesis assay. Pre-formed spheroids of lentiviral vector-transduced MDA-MB-435 cells were embedded in collagen and then stimulated with recombinant HGF to form branched tubules. Collagen invasion was quantified by scoring the mean number of tubules sprouting from each spheroid. EV, Empty Vector; DM, Decoy Met; SP, Sema-PSI. (FIG. 5C) Representative images from the experiment described in B. Magnification: 200X.

(FIG. 6A) Kaplan-Meier-like plots of tumor latency (X axis, time in days; Y axis, percent of tumor free-animals). Empty v., empty vector. (FIG. 6B) Mean tumor volume over time. (FIG. 6C) Immuno-histochemical analysis of tumor sections using anti-FLAG antibodies. Magnification: 400X. (FIG. 6D) Tumor vessel analysis. Tumor sections were stained with anti-Von Willebrand factor antibodies. The number of vessels per square mm of tumor section was determined by microscopy. EV, Empty Vector; DM, Decoy Met; SP, Sema-PSI. (FIG. 6E) Metastasis incidence analysis. Upon autopsy, serial lung sections were analyzed by microscopy to determine the presence of micrometastases. Metastasis incidence -i.e. the number of mice with metastasis over the total-is indicated in both percentage (bars) and fraction (at the end of bars). (FIG. 6F) Representative images of micrometastases from the empty vector group. Lung sections were stained with hematoxylin and eosin. Dotted lines identify the walls of blood vessels (vs). Metastatic cells (mc) can be found inside vessels as an embolus or in the parenchyma. Magnification: 400X.

DETAILED DESCRIPTION OF THE INVENTION

Figure 1:
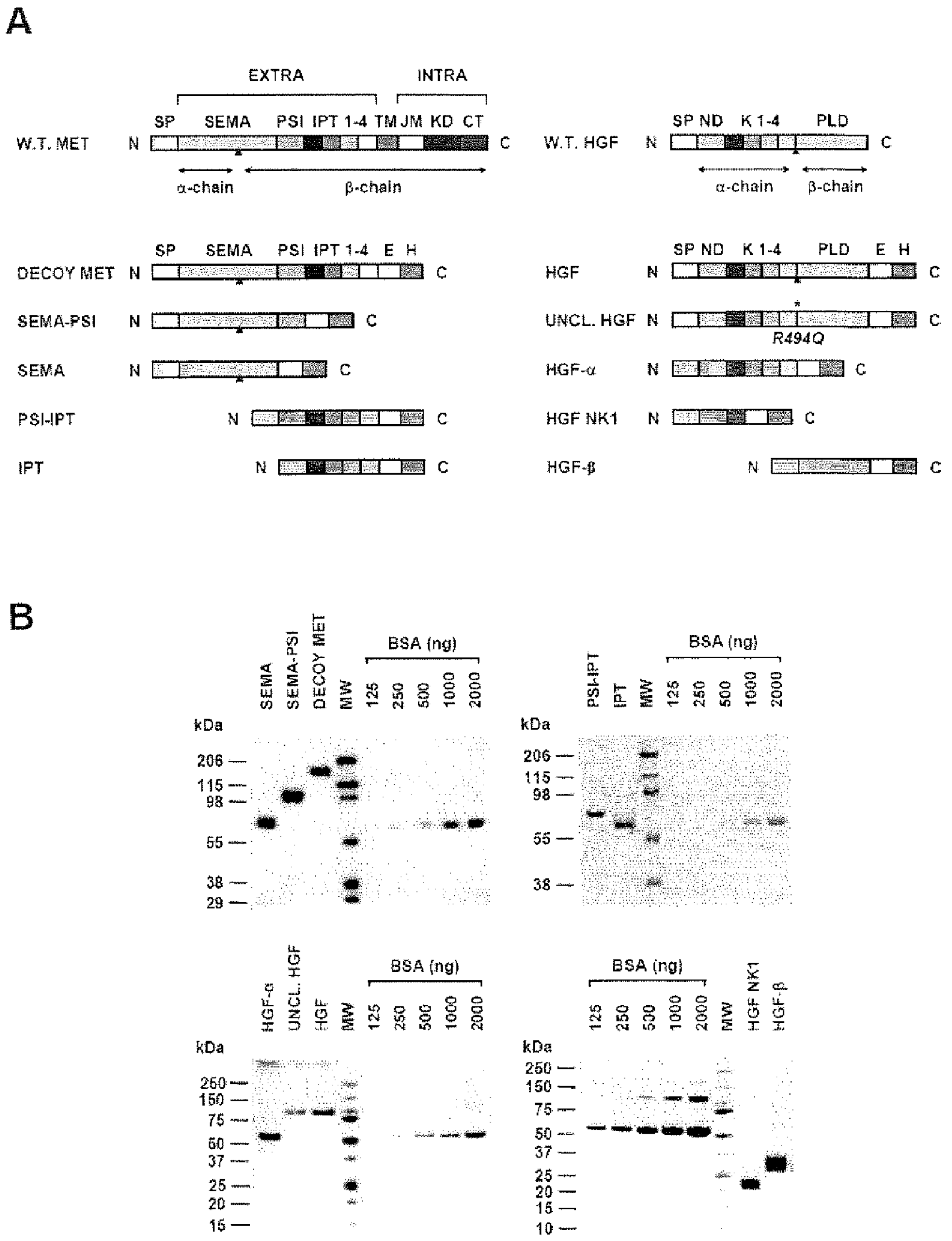
FIGS. 1A and 1B show the engineering and purification of Met and HGF subdomains.

The present invention will now be described in detail in relation to some preferred embodiments by way of non-limiting examples with reference to the annexed drawings, wherein:

FIG. 1 shows the engineering and purification of Met and HGF subdomains. (A) Schematic representation of the engineered proteins used in this study. Left panel: engineered receptors. W.T. MET, wild-type Met; EXTRA, extracellular portion; INTRA, intracellular portion; SP, signal peptide; SEMA, semaphorin homology domain; PSI, plexin-semaphorin-integrin homology domain; IPT 1-4, immunoglobulin-plexin-transcription factor homology domain 1-4; TM, trans-membrane domain; JM, juxta-membrane domain; KD, kinase domain; CT, C-terminal tail; E, FLAG or MYC epitope; H, poly-histidine tag. The red triangle indicates the proteolytic cleavage site between the α- and β-chain. Right panel: engineered ligands. W.T. HGF, wild-type HGF; ND, N-domain, K 1-4, kringle 1-4; PLD, protease-like domain; UNCL. HGF, Uncleavable HGF. The asterisk indicates the R494Q amino acid substitution in the proteolytic site. (B) Coomassie staining of affinity-purified receptors and ligands. Each protein group (Sema, Sema-PSI, Decoy Met; PSI-IPT, IPT; HGF-α, Uncleavable HGF, HGF; HGF NK1, HGF-β) has been resolved by SDS-PAGE in non-reducing conditions and is quantified against a standard curve of bovine serum albumin (BSA). MW, molecular weight marker; kDa, kilo-Dalton.

Figure 2:
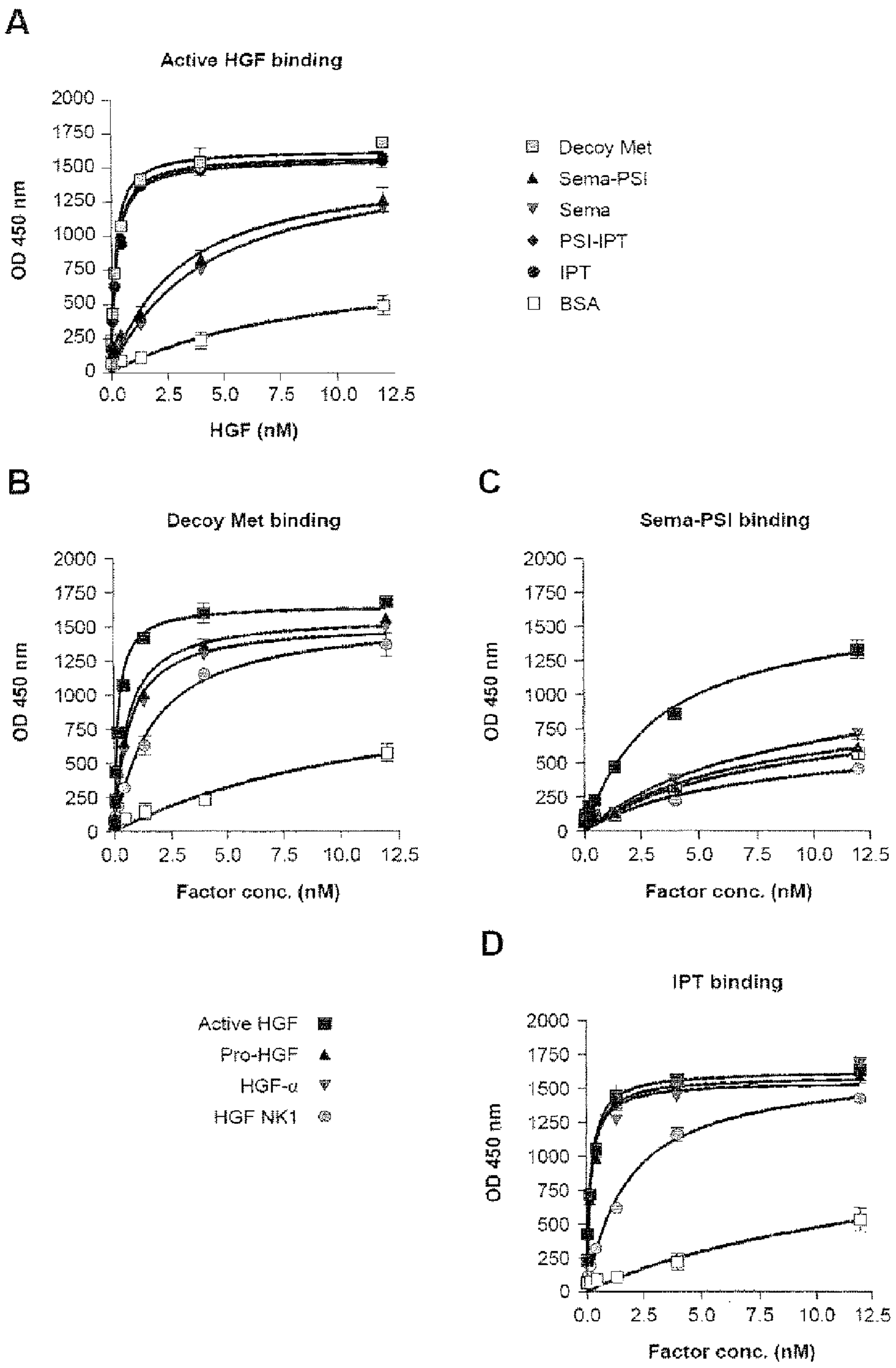
FIGS. 2A-2D show an ELISA analysis of HGF-Met interactions.

FIG. 2 shows an ELISA analysis of HGF-Met interactions. (A) Binding of Met sub-domains to active HGF. Engineered receptors were immobilized in solid phase and exposed to increasing concentrations of active HGF in liquid phase. Binding was revealed using anti-HGF antibodies. Non-specific binding was measured by using BSA instead of purified receptors in solid phase. (B, C, D) Binding of Decoy Met, Sema-PSI, and IPT to different forms of HGF. Engineered receptors were immobilized in solid phase and exposed to increasing concentrations of MYC-tagged active HGF, pro-HGF, HGF-α or HGF NK1 in liquid phase. Binding was revealed using anti-MYC antibodies. Non-specific binding was measured by using MYC-tagged angiostatin (AS) in liquid phase.

Figure 3:
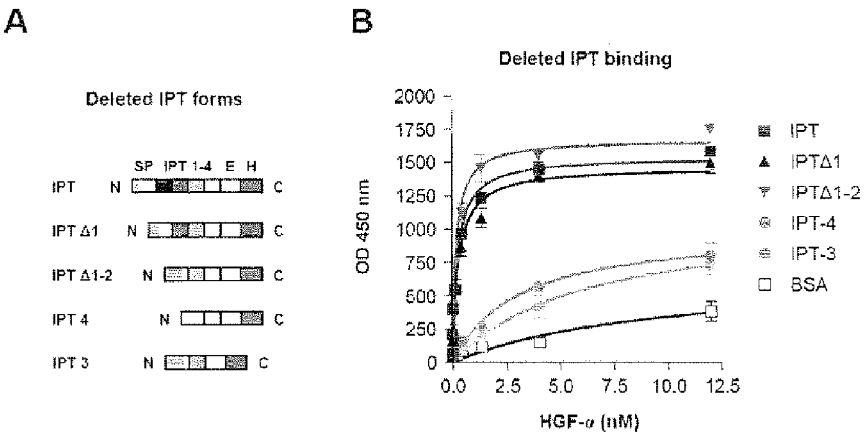
FIGS. 3A and 3B show that IPT domains 3 and 4 are sufficient to binding to HGF-α at high affinity.

FIG. 3 shows that IPT domains 3 and 4 are sufficient to binding to HGF-a at high affinity. (A) Schematic representation of deleted IPT variants. Color code and legend as in FIG. 1A. (B) ELISA analysis of interactions between IPT variants and HGF-α. Engineered IPTs were immobilized in solid phase and exposed to increasing concentrations of HGF-α in liquid phase. Binding was revealed using anti-HGF antibodies.

Figure 4:
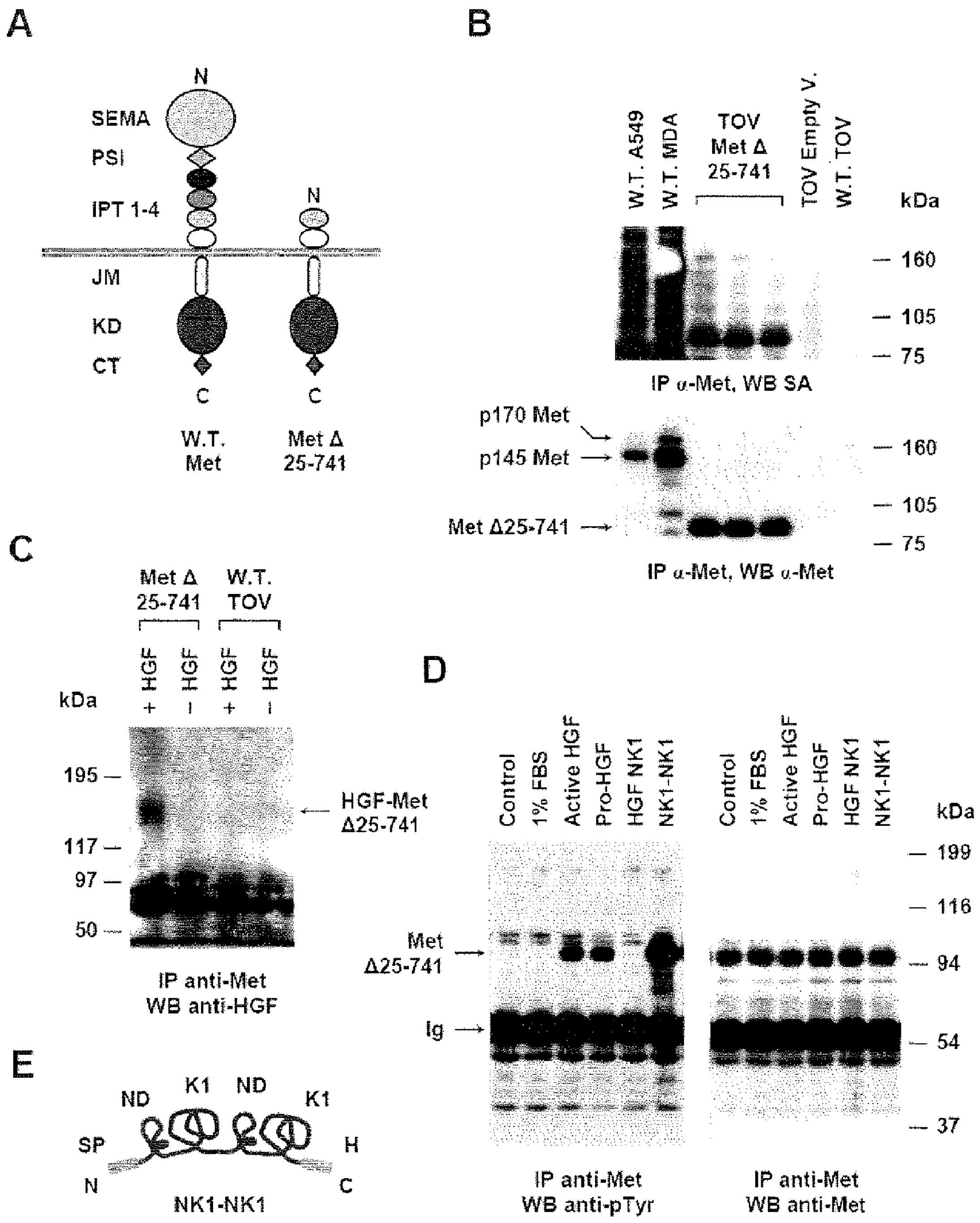
FIGS. 4A-4E show that IPT domains 3 and 4 are sufficient for binding to HGF in living cells.

FIG. 4 shows that IPT domains 3 and 4 are sufficient for binding to HGF in living cells. (A) Schematic representation of the deleted MetΔ25-741 receptor. Color code and legend as in FIG. 1A. (B) Surface biotinylation analysis. Cellular proteins were immuno-precipitated (IP) using antibodies directed against the C-terminal portion of Met and analyzed by Western blotting (WB) using horseradish peroxidase-conjugated streptavidin (SA). The same blots were re-probed with anti-Met antibodies. W.T., wild-type, A549, A549 human lung carcinoma cells; MDA, MDA-MB-435 human melanoma cells; TOV, TOV-112D human ovary carcinoma cells; Empty V., empty vector. The p170 band corresponds to unprocessed Met; p145 is the mature form of the receptor. (C) Chemical cross-linking analysis. TOV-112D cells expressing $Met_{\Delta 25-741}$ (Met Δ25-741) and wild-type TOV-112D cells (W.T. TOV) were incubated with HGF and then subjected to chemical cross-linking. Cell lysates were immuno-precipitated using anti-Met antibodies and analyzed by Western blotting using anti-HGF antibodies. Arrow indicates HGF-$Met_{\Delta 25-741}$ complexes. (D) Met phosphorylation analysis. TOV-112D cells expressing $Met_{\Delta 25-741}$ were stimulated with 1% FBS as a negative control and with equal amounts of HGF, pro-HGF, HGF NK1 or NK1-NK1. Receptor phosphorylation was determined by immuno-precipitation with anti-Met antibodies and Western blotting with anti-phosphotyrosine (anti-pTyr) antibodies. The same blots were re-probed using anti-Met antibodies. Arrows indicate bands corresponding to $Met_{\Delta 25-741}$ or immunoglobulins (Ig). (F) Schematic representation of NK1-NK1. From N- to C-terminus: SP, signal peptide; ND, N-domain; K1, kringle 1, H, poly-histidine tag.

Figure 5:
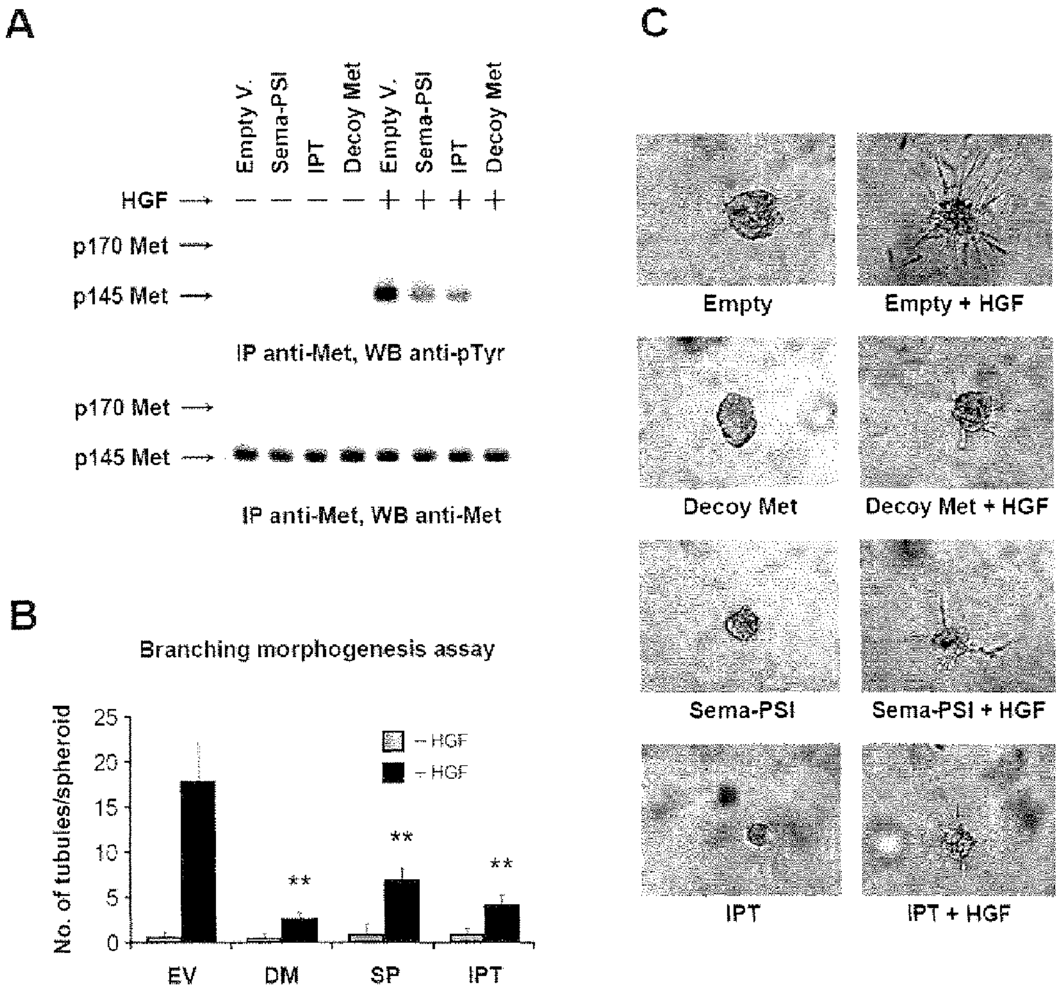
FIGS. 5A-5C show that soluble IPT inhibits HGF-induced invasive growth in vitro.

FIG. 5 shows that soluble IPT inhibits HGF-induced invasive growth in vitro. (A) Lentiviral vector transduced MDA-MB-435 cells were stimulated with recombinant HGF and Met phosphorylation was determined by immuno-blotting using anti-phosphotyrosine antibodies (upper panel). The same blot was re-probed using anti-Met antibodies (lower panel). Empty V., Empty Vector. (B) Branching morphogenesis assay. Pre-formed spheroids of lentiviral vector-transduced MDA-MB-435 cells were embedded in collagen and then stimulated with recombinant HGF to form branched tubules. Collagen invasion was quantified by scoring the mean number of tubules sprouting from each spheroid. EV, Empty Vector; DM, Decoy Met; SP, Sema-PSI. (C) Representative images from the experiment described in B. Magnification: 200×.

Figure 6:
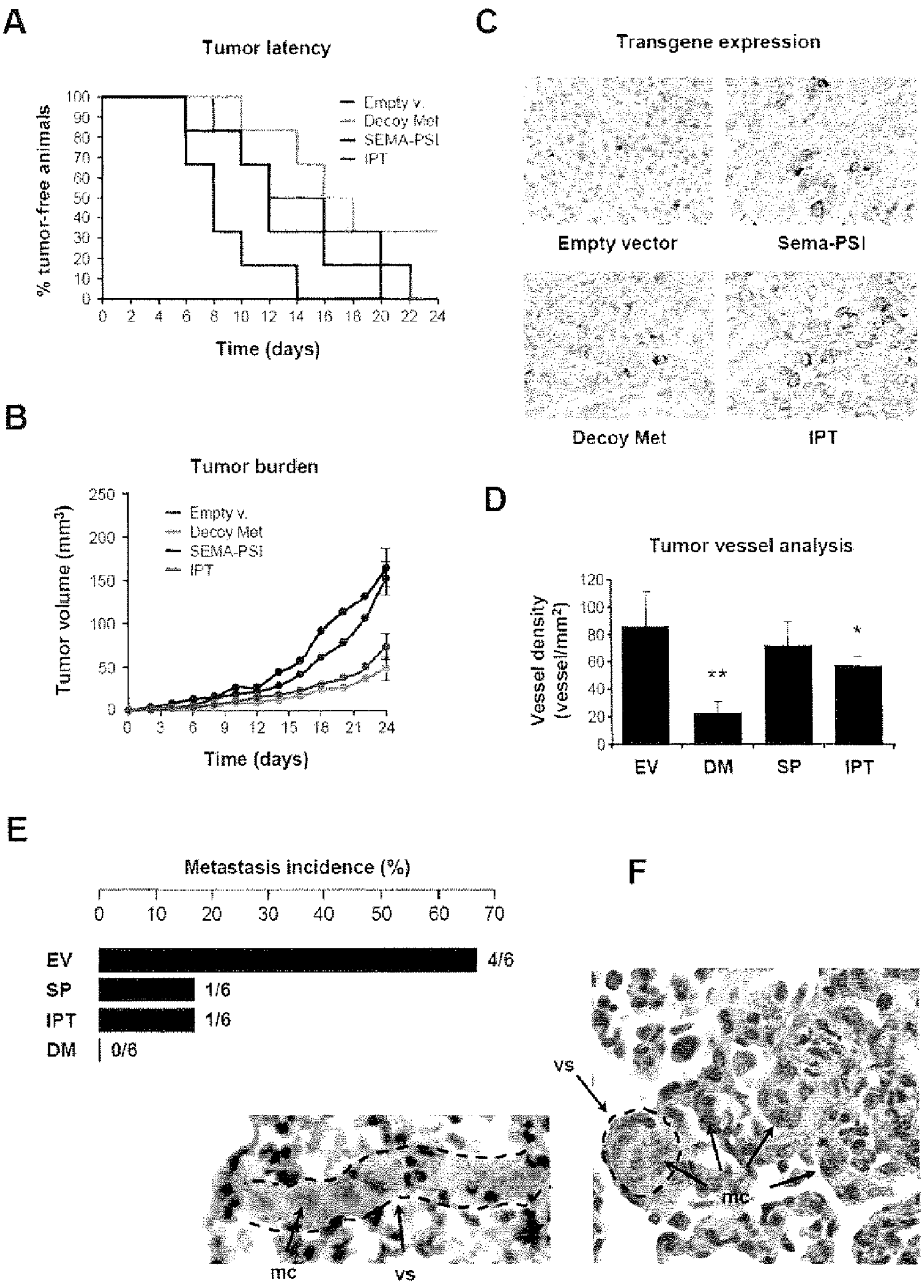
FIGS. 6A-6F show that soluble IPT displays anti-tumor and anti-metastatic activity in mice. CD-1 nu-/- mice were injected subcutaneously with lentiviral vector-transduced MDA-MB-435 cells, and tumor growth was monitored over time.

FIG. 6 shows that soluble IPT displays anti-tumor and anti-metastatic activity in mice. CD-1 nu−/− mice were injected subcutaneously with lentiviral vector-transduced MDA-MB-435 cells, and tumor growth was monitored over time. (A) Kaplan-Meier-like plots of tumor latency (X axis, time in days; Y axis, percent of tumor free-animals). Empty v., empty vector. (B) Mean tumor volume over time. (C) Immuno-histochemical analysis of tumor sections using anti-FLAG antibodies. Magnification: 400×. (D) Tumor vessel analysis. Tumor sections were stained with anti-Von Willebrand factor antibodies. The number of vessels per square mm of tumor section was determined by microscopy. EV, Empty Vector; DM, Decoy Met; SP, Sema-PSI. (E) Metastasis incidence analysis. Upon autopsy, serial lung sections were analyzed by microscopy to determine the presence of micrometastases. Metastasis incidence—i.e. the number of mice with metastasis over the total—is indicated in both percentage (bars) and fraction (at the end of bars). (F) Representative images of micrometastases from the empty vector group. Lung sections were stained with hematoxylin and eosin. Dotted lines identify the walls of blood vessels (vs). Metastatic cells (mc) can be found inside vessels as an embolus or in the parenchyma. Magnification: 400×.

The data presented in the present disclosure suggest that the α-chain of HGF binds to the IPT region of Met at high affinity, and that it does so independently of proteolytic processing of the ligand. They also suggest that HGF binding to IPT in the context of a trans-membrane Met lacking the Sema domain is sufficient for transmitting the signal for receptor activation to the cytoplasmic kinase domain, although without distinction between the inactive and active form of the ligand. Finally, they provide evidence that engineered proteins derived from the IPT region and Sema domain of Met are capable of neutralizing the pro-invasive activity of HGF both in vitro and in vivo.

It has been known for long time that HGF is a bivalent factor. Early protein engineering studies identified a high affinity Met-binding site in the N domain and first kringle of HGF. Subsequently, combined biochemical and biological analysis demonstrated that the HGF serine protease-like domain (β-chain), while not necessary for binding, plays a key role in mediating receptor activation. More recently, detailed crystallographic and mutagenesis data have thoroughly characterized both structurally and functionally the low affinity Met-binding site on the β-chain of HGF and its interaction with the Sema domain of Met. The interface between the α-chain of HGF and Met had remained however elusive. Small angle X-ray scattering and cryo-electron microscopy studies suggested the presence of contacts among the N-terminal and first kringle domain of HGF and the Sema domain of Met. However, plasmon resonance analysis revealed that this interaction has a very low affinity (about 2 times lower than that of HGF-β for Sema and 100 times lower than that of HGF-α for the intact receptor). Since this weak interaction cannot account per se for the tight bond between HGF and Met, the high affinity HGF-binding site on Met had still to be identified.

The results presented here contribute to fill this gap and suggest that this long sought-after HGF-binding site lies in the IPT region of Met and more precisely in the last two immunoglobulin like domains close to the cell membrane. Several distinct experimental evidences provided in the present disclosure suggest that this is the case. Firstly, a soluble, deleted Met receptor containing nothing but the four IPT domains (IPT) binds to HGF with substantially the same affinity as the entire extra-cellular portion of Met. Conversely, Sema displays very low affinity towards HGF. Secondly, IPT binds to active HGF, pro-HGF or HGF-A with unchanged strength. Thirdly, deletion of IPT 1 and IPT 2 does not affect the affinity of IPT for any form of HGF. Fourthly, an engineered Met receptor carrying a large deletion in its ectodomain corresponding to the Sema domain, the PSI module and the first two immunoglobulin-like domains ($Met_{\Delta 25-741}$) retains the ability to bind to HGF and to transduce the signal for kinase activation to the inside of the cell, although it cannot distinguish between active HGF and Pro-HGF. Finally, a dimeric form of HGF NK1, which is known to contain the minimal Met binding domain of HGF-α, is capable of eliciting activation of $Met_{\Delta 25-741}$ as efficiently as if not more powerfully than HGF, thus identifying in IPT 3-4 the HGF NK1-binding site.

While these data point at a key role of IPT in HGF binding, it is noteworthy that two previous structure/function studies on the extracellular portion of met failed to identify any ligand binding site in this region. A first draft of the Met ectodomain map suggested that the Sema domain is necessary and sufficient for HGF binding based on ELISA assays. A second study analyzed the role of the Sema domain in receptor dimerization and suggested that an engineered form of the Met extracellular portion containing a deletion in the Sema domain was not capable of co-precipitating HGF.

The present disclosure further demonstrates that cooperation between Sema and IPT is observed also when the extracellular portion of met is used as a biotechnological tool to inhibit HGF-induced invasive growth. In the in vitro analysis and in mouse xenografts both the IPT and Sema-PSI soluble proteins displayed a significant inhibitory effect. However, none of them could achieve the powerful inhibition displayed by the full Met ectodomain, which contains both the low affinity and high affinity HGF-binding site. This implies that both of these interactions contribute to controlling Met activity. While the HGF-β-Sema contact had already been identified as a target for therapy, the results presented here unveil a second interface that offers opportunities for pharmacological intervention. Recombinant proteins or antibodies that bind to the IPT region in place of bona fide HGF have an application as highly competitive inhibitors of Met for the treatment of HGF/Met-dependent cancers.

Materials and Methods

Protein Engineering

Soluble or trans-membrane receptors and engineered ligands described in this work have been generated by standard PCR and genetic engineering techniques. All factors conserve the leader sequence of their parental protein at the N-terminus. The amino acid (aa) sequences of soluble Met proteins (Gene Bank N. X54559) correspond to aa 1-24 (signal peptide) plus: Decoy Met, aa 25-932; Sema, aa 25-515; Sema-PSI, aa 25-562; PSIIPT, aa 516-932; IPT, aa 563-932; IPT Δ1, aa 657-932; IPT Δ1-2, aa 742-932; IPT-3, aa 742-838; IPT-4, aa 839-932. At the C-terminus of each molecule a double FLAG (SDYKDDDDK—SEQ ID No.:19) or single MYC (EQKLISEEDLN—SEQ ID No.:20) epitope sequence and a poly-histidine tag (HHHHHHH—SEQ ID No.:21) were added for protein detection and purification. The trans-membrane engineered MetΔ25-741 is identical to wild-type Met except for the deleted region (aa 25-741). The amino acid sequences of engineered HGF proteins (Gene Bank N. M73239) correspond to aa 1-31 (signal peptide) plus: HGF, aa 32-728; HGF-α, aa 32-473; HGF NK1, aa 32-205; HGF-β, aa 495-728. The above MYC or FLAG epitope and poly-histidine tag were added at the C-terminus. Uncleavable HGF has been described before (Mazzone, M. et al. (2004) *J Clin Invesn.* 114(10), 1418-1432). NK1-NK1 is a dimeric form of HEGF NK1 consisting of the same N-terminal region HGF repeated in tandem (aa 1-205 directly linked to aa 32-205 without spacer). The cDNAs encoding all engineered proteins were subcloned into the lentiviral transfer vector pRRLsin.PPT.CMV.eGFP.Wpre (SEQ ID No.:1) in place of the gfp cDNA as disclosed in Follenzi, A. et al. (2000) *Nat Genet.* 25(2), 217-222. The GFP coding sequence was replaced by the following cDNAs: decoy met FLAG.his (SEQ ID No.:2), Sema FLAG.his (SEQ ID No.:3), Sema-PSI FLAG.his (SEQ ID No.:4), PST-IPT FLAG.his (SEQ ID No.: 5), IPT FLAG.his (SEQ ID No.:6), IPT Δ1 FLAG.his (SEQ ID No.:7), IPT Δ1-2 FLAG.his (SEQ ID No.:8), IPT 3 FLAG.his (SEQ ID No.:9), IPT 4 FLAG.his (SEQ ID No.: 10), Met Δ25-741 (SEQ ID No.:11), HGF MYC his (SEQ ID No.:12), HGF-α MYC his (SEQ ID No.:13), HGF-NK1 MYC his (SEQ ID No.:14), HGF-β MYC his (SEQ ID No.: 15), uncleavable HGF MYC his (SEQ ID No.:16), NK1-NK1 his (SEQ ID No.:17), angiostatin NYC his (SEQ ID No.:18).

Enzyme-Linked Immunosorbant Assays

All engineered receptors and factors were collected from the conditioned medium of lentiviral vector-transduced MDA-MB-345 human melanoma cells in the absence of serum. Factor purification was performed by immobilized-metal affinity chromatography as previously described in Michieli P. et al. (2002) *Nat Biotechnol.* 20(5), 488-495. Conversion of pro-HGF into active HGF was performed by incubating purified pro-HGF (maximal concentration 100 ng/μl) with 2-10% FBS (Sigma, St. Louis, Mo.) at 37° C. for 24 hours. Factor conversion was analyzed by Western blotting using anti-HGF antibodies (R&D Systems, Minneapolis, Minn.). Uncleavable HGF subjected to the same incubation with FBS was used as pro-HGF in all assays that compared active HGF with unprocessed HGF. Binding of engineered ligands to soluble receptors was measured by ELISA using FLAG-tagged soluble receptors in solid phase and MYC-tagged engineered ligands in liquid phase. A fixed concentration of purified soluble receptor (100 ng/well) was adsorbed to 96-well ELISA plates. Protein-coated plates were incubated with increasing concentrations of engineered ligands, and binding was revealed using biotinylated anti-HGF antibodies (R&D Systems, Minneapolis, Minn.) or anti-MYC antibodies (Santa Cruz Biotechnology, Santa Cruz, Calif.). Binding data were analyzed and fit using Prism software (Graph Pad Software, San Diego, Calif.).

Cell Culture

MDA-MB-435 human melanoma cells were purchased from the Georgetown University Tissue Culture Shared Resource (Washington, District of Columbia). Cells were maintained in DMEM supplemented with 10% FBS (Sigma). TOV-112D human ovarian carcinoma cells were obtained from ATCC (Rockville, Md.; ATCC N. CRL-11731) and were cultured using a 1:1 mixture of MCDB 105 Medium and Medium 199 supplemented with 15% BBS (all from Sigma). A549 human lung carcinoma cells were also obtained from ATCC (ATCC N. CCL-185) and maintained in RPMI supplemented with 10% FBS.

Lentiviral Vectors

Vector stocks were produced by transient transfection of 293T cells as previously described in Follenzi, A. et al. (2000) *Nat Genet.* 25 (2), 217-222. Briefly, the plasmid DNA mix for transfection was prepared as follows: ENV plasmid (VSV-G), 9 μg; PACKAGING plasmid pMDLg/pRRE 16.2 μg; REV plasmid, 6.25 μg; TRANSFER VECTOR (plasmid #2-18), 37.5 μg. The plasmids were diluted in a solution of TE/$CaCl_2$, to which a HBS solution was added while vortexing at maximum speed. The DNA/$CaCl_2$/HBS mix was immediately added drop-wise to the cell plates that were then incubated at 37° C. After 14-16 hours the culture medium was replaced with a fresh one. Cell culture supernatants containing vector particles were collected about 36 hours after medium changing. After collection, the supernatants were filtered through 0.2 μm pore membranes and stored at −80° C. Viral p24 antigen concentration was determined by the HIV-1 p24 core profile ELISA kit (NEN Life Science Products, Boston, Mass.) according to the manufacturer's instructions. Cells were transduced in six-well plates ($10^5$ cells/well in 2 ml of medium) using 40 ng/ml of p24 in the presence of 8 μg/ml polybrene (Sigma) as described in Vigna, E. and Naldini, L. (2000) *J Gene Med.* 2(5), 308-316. Medium was changed about 18 hours after transduction. Cell growth and protein production was monitored over time. Transduced cell lines were then seeded in 15 cm plates, grown to 80% confluence and incubated in medium without serum. After 72 hours, the supernatants containing the recombinant soluble proteins were collected, filtered and purified by affinity chromatography or stored at −30° C.

Immuno-Precipitation and Western Blot Analysis

Cell lysis, immuno-precipitation and Western blot analysis were performed using extraction buffer (EB) as described in Longati, P. et al. (1994) *Oncogene* 9(1), 49-57. Signal was detected using ECL system (Amersham Biosciences, Piscataway, N.J.) according to the manufacturer's instructions. Anti-Met antibodies for immunoprecipitation have been described by Ruco, L. P. et al. (1996) *J Pathol.* 180(3), 266-270 and were purchased from UBI (Lake Placid, N.Y.). Anti-Met antibodies for Western blot were purchased from Santa Cruz. Anti-FLAG antibodies were obtained from Sigma. Met phosphorylation analysis in lentiviral vector transduced MDA-MB-435 cells was performed as previously described in Michieli, P. et al. (2004) *Cancer Cell* 6(1), 61-73.

HGF Cross-Linking and Met Activation Analysis

Lentiviral vector-transduced TOV-112D cells expressing $Met_{\Delta 25-741}$ were subjected to surface biotinylation analysis using an ECL™ Surface Biotinylation Module kit (Amersham Biosciences) according to the manufacturer's instructions. Chemical cross-linking was performed as previously described in Mazzone, M. et al. (2004) *J Clin Invest.* 114(10), 1418-1432. Briefly, cells were deprived of serum growth factors for 3 days and then incubated with 1 μM HGF for 3 hours. Cell lysates were immuno-precipitated using antibodies directed against the C-terminal portion of Met as disclosed in Ruco, L. P. et al. (1996) *J Pathol.* 180(3), 266-270, resolved by SDS-PAGE using a 3-10% polyacrylamide gradient and analyzed by Western blotting using anti-HGF antibodies (R&D). For receptor activation analysis, TOV-112D cells expressing $Met_{\Delta 25-741}$ were deprived of serum growth factors for 3 days and then stimulated with 1 nM HGF, Uncleavable HGF, HGF Nk1 or NK1-NK1 for 10 minutes. Cells were lysed using EB as described in Longati, P. et al. (1994) *Oncogene* 9(1), 49-57. Cellular proteins were immuno-precipitated with anti-met antibodies as above and analyzed by Western blotting using anti-phosphotyrosine antibodies (UBI). The same blots were re-probed with anti-Met antibodies (Ruco, L. P. et al. (1996) *J Pathol.* 180(3), 266-270).

Biological Assays

Collagen invasion assays using MDA MB-435 cells were performed using preformed spheroids as described in Michieli, P. et al. (2004) *Cancer Cell* 6(1), 61-73, Briefly, spheroids were generated by incubating cells overnight (700 cells/well) in non-adherent 96-well plates (Greiner, Frickenhausen, Germany) in the presence of 0.24 g/ml methylcellulose (Sigma). Spheroids were embedded into a collagen matrix containing 1.3 mg/ml type I collagen from rat tail (BD Biosciences, Bedford, Mass.) and 10% FBS using 96-well plates (40 spheroids/well), Embedded spheroids were cultured at 37° C. for 24 hours, and then stimulated with 30 ng/ml HGF (R&D) or no factor for additional 24 hours. The number of tubules sprouting from each spheroid was scored by microscopy. At least 12 spheroids per experimental point were analyzed.

Tumorigenesis Assays

Lentiviral vector-transduced MDA-MB-435 tumor cells ($3 \cdot 10^6$ cells/mouse) in 0.2 ml of DMEM were injected subcutaneously into the right posterior flank of six-week old immunodeficient nu−/− female mice on Swiss CD-1 background (Charles River Laboratories, Calco, Italy). Tumor size was evaluated every 2 days using a caliper. Tumor volume was calculated using the formula $V=4/3\pi x2y/2$ where x is the minor tumor axis and y the major tumor axis. A mass of 15 $mm^3$-corresponding approximately to the initial volume occupied by injected cells was chosen as threshold for tumor positivity. Mice whose tumors were below this threshold were considered tumor-free. After approximately 4 weeks, mice were euthanized and tumors were extracted for analysis. Animals were subjected to autopsy. Tumors and lungs were embedded in paraffin and processed for histology. Micrometastasis analysis was performed by microscopy on serial lung sections stained with hematoxylin and eosin. Tumor sections were stained with hematoxylin and eosin and analyzed by an independent pathologist not informed of sample identity. Transgene expression was determined on tumor sections by immuno-histochemistry using anti-FLAG antibodies (Sigma). Sections were counterstained with Meyer hematoxylin (Sigma). Tumor angiogenesis was analyzed by immuno-histochemistry using anti-Von Willebrand factor antibodies (DAKO, Glostrup, Denmark). Sections were counterstained as above. Vessel density was assessed by microscopy. At least 12 fields per animal were analyzed. All animal procedures were approved by the Ethical Commission of the University of Turin, Italy, and by the Italian Ministry of Health.

Statistical Analysis

Statistical significance was determined using a two-tail homoscedastic Student's t-Test (array 1, control group; array 2, experimental group). For all data analyzed, a significance threshold of $p<0.05$ was assumed, In all figures, values are expressed as mean±standard deviation, and statistical significance is indicated by a single ($p<0.05$) or double ($p<0.01$) asterisk.

Results

Engineering of HGF/Met Functional Domains

A schematic representation of the functional domains contained in Met and HGF is shown in FIG. 1A. The extracellular portion of Met includes a Sema domain, a PSI hinge, and four IPT modules (left panel). HGF is composed of an α- and a β-chain joined by a disulphide bridge in the mature protein. The α-chain in turn comprises an N-terminal domain and four kringles (right panel). To analyze the interactions between Met and HGF, the inventors expressed all these functional domains as individual, soluble proteins. Functional domains were engineered to contain the signal peptide of the parental protein at their N-terminus, so that they could be properly secreted. At the C-terminus, an exogenous epitope (FLAG or MYC) for antibody recognition and a poly-histidine tag for protein purification were added. All cDNAs encoding the engineered factors were subcloned into the lentiviral vector pRRLsin.PPT.CMV.Wpre, and recombinant lentiviral particles were produced as described in Materials and Methods. Recombinant proteins were collected from the conditioned medium of lentiviral vector-transduced MDA-MB-435 human melanoma cells and purified to homogeneity by affinity chromatography. Purified proteins were quantified against standards by SDS-PAGE (FIG. 1B).

ELISA Analysis of Met-HGF Interactions

The ability of Met ectodomains to interact with HGF was tested in ELISA binding assays. Soluble receptors (Decoy Met, Sema-PSI, Sema, PSI-IPT, IPT) were immobilized in solid-phase and exposed to increasing concentrations of active HGF. Binding was revealed using biotinylated anti-HGF antibodies. Non-specific HGF binding was determined using bovine serum albumin (BSA) in solid phase instead of soluble Met domains Binding affinity was determined by nonlinear regression analysis as described in Materials and Methods. In these conditions, decoy Met bound to HGF with a $K_D$ of approximately 0.2-0.3 nM. Consistent with previous measurements, Sema-PSI and Sema bound to HGF with an affinity at least one log lower compared to decoy Met. Surprisingly, both PSI-IPT and IPT bound to HGF very efficiently, with almost the same affinity as decoy Met (FIG. 2A). The presence or absence of the PSI domain did not affect the binding affinity for HGF of either Sema or IPT. Since almost all Sema domains found so far in nature have a PSI module at their C-terminus, the inventors therefore continued the binding analysis using decoy Met, Sema-PST, and IPT.

To determine the affinity of each Met module for pro-HGF, HGF-α, HGF NK1 and HGF-β and to compare it with that for active HGF, engineered receptors were immobilized in solid phase and exposed to increasing concentrations of MYC-tagged ligands. Binding was revealed using anti-MYC antibodies. Non-specific binding was determined using the kringle-containing protein angiostatin (AS) also tagged with a MYC epitope—in liquid phase. Pro-HGF, HGF α-chain and HGF NK1, which represents the minimal Met-binding module of HGF α-chain, bound to Decoy Met with a 3-, 4- and 10-time reduced affinity compared to active HGF, respectively (FIG. 2B). Binding of HGF-β to decoy Met (or to any other Met domain) was too low to be detected in this kind of assay. Sema-PSI bound at a significant affinity to active HGF only, while binding to pro-HGF, HGF-α or HGF NK1 was undistinguishable from non-specific binding (FIG. 2C). In contrast, IPT bound to active HGF, pro-HGF and HGF-α with the same high affinity (FIG. 2D). HGF NK1 bound to IPT 10 times less tightly than active HGF, i.e. with the same affinity as it bound to Decoy Met. These data suggest that the IPT region of Met binds to the α-chain of HGF at high affinity independently of proteolytic processing of the ligand.

The α-Chain of HGF Binds to IPT Domains 3 and 4 with High Affinity

The IPT region of Met extends for about 400 amino acids and contains four IPT domains. To more finely map the IPT-HGF interface, a series of IPT variants that were deleted in one or more domains were engineered (FIG. 3A). IPT Δ1 and IPT Δ1-2 are two N-terminal deleted forms of IPT lacking the first or the first two immunoglobulin-like domains, respectively. IPT-3 and IPT-4 correspond to the two C-terminal immunoglobulin-like domains expressed as single proteins. Protein production and purification were performed as described above. The ability of the engineered IPTs to interact with HGF α-chain was investigated in ELISA binding assays using the whole IPT region as a control. IPT, IPT Δ1, IPT Δ1-2, IPT-3 and IPT-4 were immobilized in solid phase and exposed to increasing concentrations of HGF-α. Binding was revealed using anti-HGF antibodies. Non-specific binding was measured using BSA as above. As shown in FIG. 3B, deletion of the first two immunoglobulin-like domains did not substantially affect HGF binding.

In fact, IPT Δ1-2, a protein corresponding to the last two immunoglobulin-like domains of Met, bound to the α-chain of HGF with equal if not higher strength than IPT. However, further deletion of either the third or fourth immunoglobulin-like domain did almost completely impair HGF-α binding. Similar results were obtained using active HGF or pro-HGF instead of HGF-α. These data suggest that the last two immunoglobulin-like domains of Met, that lie close to the transmembrane helix in the context of a bona fide Met, are sufficient for binding the α-chain of HGF at high affinity.

IPT Domains 3 and 4 are Sufficient for Binding to HGF in Living Cells.

To determine whether HGF could bind to IPT 3 and 4 in the context of a membrane-anchored receptor, a Met protein carrying a large deletion in the extracellular region was engineered. Amino acids 25-741, corresponding to the Sema domain (aa 25-515), the PSI domain (aa 516-562) and the first two IPT domains (IPT 1 and 2, aa 563-741) were deleted, generating a recombinant receptor TO containing IPT domains 3 and 4, the transmembrane helix and the full cytoplasmic region (FIG. 4A). The cDNA encoding the engineered receptor $Met_{\Delta 25-741}$ was subcloned into the same lentiviral vector described above. Recombinant lentiviral particles were used to transduce the human ovary carcinoma cell line TOV-112D, which lacks endogenous Met expression as determined by RT-PCR analysis (Michieli, P., et al. (2004) *Cancer Cell* 6(1), 61-73). Surface biotinylation analysis revealed that $Met_{\Delta 25-741}$ was properly expressed and exposed on the membrane of TOV-112D cells (FIG. 4B).

To examine whether $Met_{\Delta 25-741}$ could bind to HGF, lentiviral vector-transduced cells were incubated in the presence or absence of recombinant HGF and subsequently treated them with the cross-linking agent BS3. Cell lysates were immuno-precipitated with an antibody raised against the C-terminal portion of Met, resolved by SDS PAGE and analyzed by western blotting using anti-HGF biotinylated antibodies. As a control, the same analysis was performed on wildtype TOV-112D cells. Immunoblots showed a distinct band with a molecular weight of approximately 180 kD in the lane corresponding to cells expressing $Met_{\Delta 25-741}$ treated with HGF but not in lanes corresponding to the same cells without HGF or to wild-type TOV-112D cells, either in the presence or absence of the ligand (FIG. 4C). Considering that both $Met_{\Delta 25-741}$ and HGF have a molecular weight of approximately 90 kDa, the immuno-precipitated cross linked protein is compatible with a complex formed by HGF plus $Met_{\Delta 25-741}$.

HGF Binding to IPT Domains 3 and 4 Results in Met Activation in Living Cells.

The inventors next tested whether HGF binding to $Met_{\Delta 25-741}$ could induce Met kinase activation. To this end, lentiviral vector transduced TOV-112D cells were stimulated with pro-HGF or active HGF, and cell lysates were immuno-precipitated with anti-Met antibodies as above. Receptor activation was determined by Western blot analysis using anti-phosphotyrosine antibodies. The same blots were re-probed with anti-Met antibodies to normalize the amount of receptor immuno-precipitated. Remarkably, both pro-HGF and active HGF were capable of inducing robust phosphorylation of $Met_{\Delta 25-741}$ (FIG. 4D). Since pro-HGF binding to full-size Met does not induce kinase activation, this suggests that the Sema domain somehow exerts an auto-inhibitory effect on Met catalytic activity that is released upon binding to active HGF. Receptor stimulation was also performed using HGF NK1 and an engineered dimeric ligand consisting of two NK1 fragments repeated in tandem (NK1-NK1; FIG. 4E). As shown in FIG. 4D, NK1-NK1 stimulation of lentiviral vector-transduced TOV-112D cells resulted in potent phosphorylation of $Met_{\Delta 25-741}$, while stimulation with monomeric NK1 had no effect. These results suggest that the two C-terminal IPT domains of Met (IPT 3 and 4) are sufficient to bind to HGF (and more precisely to HGF NK1 that represents the minimal met-binding module in the $\alpha$-chain of HGF) and to transmit the signal for receptor activation to the cytoplasmic kinase domain, presumably following ligand-induced receptor dimerization. However, they also suggest that IPT 3 and 4 alone are not sufficient for distinguishing the biologically active form of HGF from its inactive precursor, pro-HGF.

Soluble IPT Inhibits HGF-Induced Invasive Growth In Vitro.

In a previous study, it has been demonstrated that the extracellular portion of Met expressed as a soluble protein (Decoy Met) inhibits HGF-induced invasive growth both in vitro and in mouse models of cancer (Michieli P. et al. (2004) *Cancer Cell* 6(1), 61-73). Recombinant soluble Sema-PSI was also shown to inhibit both ligand-dependent and -independent Met phosphorylation (Kong-Beltran M. et al. (2004) *Cancer Cell* 6 (1), 75-84). Based on these results, it has been tested whether soluble IPT displayed HGF/Met antagonistic activity in living cells. MDA-MB-435 human melanoma cells, which express Met and are an established model system for analysis of HGF-mediated invasive growth, were transduced with lentiviral vectors encoding soluble Decoy Met, Sema-PSI or IPT. Cells transduced with an empty vector were used as control. Lentiviral vector-transduced cells secreting comparable levels of soluble factors (approximately 50 pmol/$10^6$ cells/24 hours) were serum-starved for several days, allowing the recombinant factors to accumulate in the medium, and then stimulated with recombinant HGF. Met tyrosine phosphorylation was determined by immuno-blotting with anti-phosphotyrosine antibodies as described above. As shown in FIG. 5A, both IPT and Sema-PSI partially inhibited HGF-induced Met phosphorylation, while Decoy Met completely neutralized the ability of HGF to induce Met activation. Reprobing of the same immuno-blots with antibodies directed against the C-terminal tail of Met revealed no substantial difference in the amounts of immuno-precipitated protein.

To test the inhibitory potential of Met ectodomains in a more biological setting, the same cells were employed to perform an HGF-dependent branching morphogenesis assay. Preformed cell spheroids were seeded in a three dimensional collagen matrix and then stimulated with recombinant HGF to form tubular structures. Branching was quantified by scoring the mean number of tubules sprouting from each colony. As shown in FIG. 5B, both soluble IPT and Sema-PSI inhibited HGF-induced colony branching (Empty vector, 17.5 tubules/colony; IPT, 4.0 tubules/colony, Sema-PSI, 6.7 tubules/colony). However, consistent with the results obtained in phosphorylation experiments, decoy Met was a more potent HGF-inhibitor than either of its subdomain (2.5 tubules/colony). Representative images of colony morphology are shown in FIG. 5C.

Soluble IPT Displays Anti-Tumor and Anti-Metastatic Activity in Mice.

The above results prompted the present inventors to explore the therapeutic potential of soluble IPT in mouse models of cancer. Lentiviral vector-transduced MDA-MB-435 melanoma cells were injected subcutaneosly into CD-1 nu–/– mice, and tumor growth was monitored over time. After approximately three weeks, tumors were extracted for analysis, and mice were subjected to autopsy. In a Kaplan-Meier-like analysis, where the percentage of tumor-free animals is plotted against time and tumor latency is quantified calculating the median in days, all engineered soluble receptors delayed the appearance of experimental tumors. However, IPT was slightly more effective than Sema-PSI and decoy Met was more potent than either IPT or Sema-PSI (FIG. 6A). Analysis of tumor burden over time revealed that IPT was only slightly less effective than decoy Met, while Sema-PSI inhibited neoplastic growth only during the very early stages of the experiment (FIG. 6B). Immuno-histochemical analysis of transgene expression showed that Decoy Met, Sema-PSI and IPT reached similar levels and distribution in tumors (FIG. 6C).

As HGF is a potent pro-angiogenic factor, it has been determined whether inhibition of HGF/Met in tumors resulted in impairment of angiogenesis. Tumor sections were analyzed by immuno-histochemistry using antibodies against Von Willebrand factor, and vessel density was assessed by microscopy (FIG. 6D). IPT decreased tumor vessel density by 1.5 times, while decoy Met achieved a much stronger inhibition (approximately 4 times); Sema-PSI did not significantly affect tumor angiogenesis. Upon autopsy, lungs from the mice described above were extracted and processed for histology. Serial lung sections were stained with hematoxylin and eosin, and analyzed by microscopy to determine the presence of micrometastases. The results are shown in FIG. 6A. In the control group, 4 out of 6 mice (67%) were bearing micrometastases. In the IPT and Sema PSI group, micrometastases could be found in only 1 out of 6 mice (17%), while no metastasis could be found in the decoy Met group. Metastatic lesions were both parenchymal (extravascular) and embolic (intravascular; see FIG. 6F for representative images).

The identification of the high affinity HGF binding site on the HGFR provided in the present disclosure allows designing of novel procedures leading to the generation of more specific inhibitors/antagonists of HGF and of HGFR. The following are non-limiting examples of novel methods for the identification of inhibitors/antagonists of HGF/HGFR targeting the high affinity binding site of HGFR or utilizing the high affinity binding site of HGFR as a tool to generate novel inhibitors/antagonists.

Development of a Monoclonal Antibody that Binds to Extracellular IPT-3 and IPT-4 Domains of HGF Preventing HGF Binding Given that interaction of HGF with the extracellular IPT-3 and IPT-4 domains is essential for high affinity HGF binding, one can generate specific monoclonal antibodies that bind to IPT-3 and IPT-4 and compete with HGF for HGFR binding. This can be achieved by several strategies.

(A) A recombinant protein or peptide derived from IPT-3 and IPT-4 is generated by standard genetic engineering technology or chemical synthesis. This protein or peptide is injected into an appropriate laboratory animal (usually a mouse or a rat) to give rise to an immune reaction. Splenocytes are then isolated from the immunized animal and fused to a myeloma cell line, and antibody-producing hybridoma clones are selected by standard monoclonal antibody technology. Antibodies directed against IPT-3 and IPT-4 are then screened by an ELISA method similar to the ones described in this disclosure that utilizes recombinant IPT-3 and IPT-4 in solid phase and hybridoma-produced antibodies in liquid phase. Binding is revealed using anti-mouse immuno globulin antibodies that are available commercially. Alternatively, antibodies are screened for their ability to displace recombinant HGF (in liquid phase) from IPT-3 and IPT-4 (in solid phase), or for their ability to immuno-precipitate recombinant IPT-3 and IPT-4 proteins.

(B) A polynucleotide sequence coding for IPT-3 and IPT-4 inserted in an appropriate expression vector is injected directly into a laboratory animal to give rise to an immune response against the gene product. Antibodies directed against IPT-3 and IPT-4 are then isolated and screened as described above.

(C) A polynucleotide sequence coding for IPT-3 and IPT-4 inserted in an appropriate expression vector is transferred into a mammalian cell line not expressing HGFR to obtain expression of IPT-3 and IPT-4 on the cell surface. Cells expressing IPT-3 and IPT-4 are then injected into a laboratory animal to give rise to an immune response, and antibodies directed against IPT-3 and IPT-4 are isolated and screened as described above.

(D) A library of native antibodies generated by standard genetic engineering techniques (for example by the technology known as phage display) from mammalian lymphocytes (preferably human, for example from lymphocytes infiltrating a tumor expressing HGFR) is screened using recombinant IPT-3 and IPT 4 proteins. Positive clones (i.e. those clones that bind to IPT-3 and IPT-4 at high affinity) are then isolated, expanded, and the antibody characterized biochemically.

(E) Human memory B cells are isolated from the peripheral blood of a patient harboring a tumor expressing HGFR as disclosed by several studies including Traggiai E. et al. (2004) *Nat Med.* 10(8), 871-875. Once cultures of immortalized memory B cells are established, a skilled artisan in the field can screen for cells secreting an antibody directed against IPT-3 and IPT-4 using the methods described here above in (A). Having identified such antibody-producing cells, the desired antibody can be cloned by polymerase chain reaction and standard genetic engineering procedures.

Identification of a Test Compound that Binds to Extracellular IPT-3 and IPT-4 Domains of HGFR Inhibiting HGFR Activity With a different approach, it is possible to isolate test compounds of diverse origin that bind to the high affinity HGF binding site of HGFR and interfere with HGF-induced HGFR activation. This can be achieved by several strategies.

(A) Using ELISA assays similar to those described in this disclosure, a skilled artisan in the field can screen a compound library (including but not limited to a synthetic chemical library, a natural compound library, a small molecule library, a peptide library) for agents that displace HGF interaction with IPT-3 and IPT-4. In this kind of assays, recombinant IPT 3 and IPT-4 protein is immobilized in solid phase and incubated with a fixed amount of HGF in liquid phase. Following exposure to library compounds, HGF binding is measured with commercially available anti-HGF antibodies.

(B) Using a cell line expressing an engineered form of the HGFR containing nothing but the IPT-3 and IPT-4 domains in the extracellular part similar to that described in this disclosure ($Met_{\Delta 25-741}$), a skilled artisan in the field can screen a compound library (including but not limited to a synthetic chemical library, a natural compound library, a small molecule library, a peptide library) for agents that displace HGF interaction with IPT-3 and IPT-4 or inhibit HGF-induced HGFR activation. This can be achieved by putting said engineered cells in contact with the library and then measuring HGF-induced HGFR phosphorylation as described in the present study, or by other means that reveal HGFR activation including a scatter assay, a reconstituted matrix invasion assay, a branching morphogenesis assay, a cell survival assay or other in vitro biological tests as described in Michieli, P. et al. (2004) *Cancer Cell* 6(1), 61-73.

(C) Using the engineered cell line described above, a skilled artisan in the field can screen a genetic library (including but not limited to a cDNA expression library, a short hairpin RNA library, an antisense DNA library, a random nucleotide library) for polynucleotides or gene products that displace HGF interaction with IPT-3 and IPT 4 or inhibit HGF-induced HGFR activation. This can be achieved by transfecting, transducing or anyway introducing the nucleotide library into said cells and then testing the ability of HGF to activate the deleted form of HGFR expressed by the same cells. HGFR activation is measured as described in (B).

Exemplary Functional Assays that Measure the Biological Activity of Compounds that Bind to Extracellular IPT-3 and IPT-4 Domains of HGFR Whatever strategy is employed to generate anti-IPT antibodies or IPT-binding compounds, the final product (i.e. monoclonal antibodies directed against IPT-3 and IPT-4 or natural or synthetic compounds that bind to IPT-3 and IPT-4) is then subjected to biological assays aimed at determining whether these agents have the ability to interfere with HGFR activity. These assays can be performed in vitro using cultured mammalian cells or in vivo using laboratory animals.

(A) Scatter assay. Epithelial cells growing in compact colonies in a Petri dish and expressing HGFR are induced to 'scatter' by stimulation with HGF. As a result of HGF stimulation, cells in the Petri dish appear more separated and dispersed. This assay can be performed in the presence of several test compounds. Among the compounds tested, an HGF/HGFR inhibitor/antagonist can be identified by the absence of a scattered phenotype in response to HGF stimulation.

(B) Cell migration assay. Cells expressing HGFR have the ability to migrate towards an HGF gradient. In other words, cells are attracted by chemotaxis towards higher concentrations of HGF. This ability can be exploited to screen for HGF inhibitors in a Boyden chamber assay. Cells are seeded in the first chamber and HGF is applied in the second chamber that is separated from the first by a porous membrane. Cells migrate through the membrane and reach the second chamber were HGF is more concentrated. Agents that inhibit this process are identified as HGF/HGFR inhibitors/antagonists.

(C) Transwell™ migration assay or reconstituted matrix invasion assay. This is a variation of the assay described in (B) in which the porous membrane is covered with a layer of collagen, Matrigel™, or other reconstituted organic matrices. Cells have to digest the organic matrix in order to migrate through it. This is a more rigorous assay that measures invasion rather than simple migration of cells.

(D) Collagen invasion assay or branching morphogenesis assay. In this assay, mammalian cells expressing HGFR (preferably epithelial cells or carcinoma cells) are seeded in a tridimensional layer of collagen and then allowed to grow until they form spheroids of approximately 1,000 cells each. Alternatively, spheroids can be pre-formed ahead by incubating cells overnight in non-adherent 96-well plates in the presence of methylcellulose as disclosed in Michieli, P. et al. (2004) *Cancer Cell* 6(1), 61-73. Once spheroids are embedded in the collagen layer, they are stimulated with HGF and incubated at 37° C. This results in the sprouting of hollow tubules from the spheroids; each tubule is formed by several cells organized in a tubular structure and polarized so that there is a side of the cell that sees the lumen and a second side that sees the medium outside. As the assay goes on tubules tend to branch and to form a more complex architecture. This assay is highly specific for HGF. Agents that inhibit this process have a high probability to represent very specific HGF/HGFR antagonists.

(E) Mitogenic assay. HGF has the ability to induce DNA replication and cell division in some cell expressing HGFR. The most responsive cells are certainly primary hepatocytes, usually mouse or rat. To test HGF-induced DNA replication, cells are deprived of serum growth factors and then stimulated with increasing concentrations of HGF. Shortly after, radioactive thymidine is added and the cells are incubated at 37° C. for approximately one day. Following extensive washing and fixation, radioactive thymidine incorporated into cell DNA is measured by liquid scintillation counting or other standard methods that allow radiation quantification.

(F) Survival assay. HGF has the ability to protect HGFR-expressing cells against apoptosis or programmed cell death. This can be exploited to measure HGFR activity in a survival assay, Cells are preincubated with HGF and the test compound (potential HGFR inhibitor), and then subjected to an apoptotic stimulus such as a toxic drug, absence of adherence, hypoxia, heat shock, radiation, or DNA damage. After an appropriate time interval, cell death is measured by standard methods including TUNEL (Terminal deoxynucleotidyl transferase biotin-dUTP Nick End Labeling), nucleosomes, DNA ladder, caspase activity, vital dye staining or any variation thereof.

(G) Mouse tumorigenesis assay. In this kind of assay, the activity of a potential HGF/HGFR inhibitor is tested directly in a laboratory animal, preferably a mouse or a rat. There are several methods for obtaining a tumor in a mouse. The most utilized strategy is to create a xenograft, i.e. to transplant tumor cells (usually of human origin) into an animal recipient (usually an immunodeficient mouse). Cells can be implanted subcutaneously (a quick and simple method to obtain an experimental tumor) or orthotopically, i.e. in the same organ where the tumor cell has been isolated (e.g. a breast carcinoma into the mammary fat pad, a colon carcinoma into the intestine mucosa, a hepatocarcinoma into the liver parenchyma and so on). Whatever the method employed is, injection of tumor cells into a laboratory animal gives rise to an experimental tumor. This tumor-bearing animal can now be used to evaluate the anti-tumor potential of test compounds. Anti-HGF/HGFR antibodies or compounds can be delivered to an animal carrying a tumor lesion with dysregulated HGF/HGFR signaling by the most appropriate existing method including intravenous injection, intraperitoneal injection, osmotic pump, oral administration, suppository, gene therapy protocol, local administration and so on. After an appropriate treatment period, the animal is euthanized and its tumor and organs are explanted for analysis.

(H) Mouse metastogenesis assay. Experimental metastases can be induced in a mouse by systemic injection of tumor cells. These get entrapped in the lung capillaries and subsequently extravasate to give rise to pulmonary metastases. These can be measured upon autopsy by several approaches including microscopy, histological analysis, immuno-histochemical methods, whole-body imaging. The test compounds are delivered as described in (G).

(I) Gene therapy protocol. In case the HGF/HGFR inhibitor is an antibody, a recombinant protein, a peptide or a small interfering RNA, delivery to the tumor-bearing animal can be achieved by a gene therapy approach. This consists in introducing the desired polynucleotide into an appropriate delivery vector that can be chosen among lentiviral vectors, adenoviral vectors, retroviral vectors, naked DNA, or any variation thereof. The vector preparation can be delivered sytemically or locally to the tumor depending on the tumor site, on the vector or on the tumor histotype. The biological effects of gene therapy are analyzed as described for other compounds in (G).

The invention claimed is:

1. A method to detect the ability of a test agent to act as an antagonist/inhibitor of hepatocyte growth factor receptor useful in the treatment of cancer, comprising the steps of:

(a) putting in contact a test agent with i) a polypeptide consisting of the extra-cellular IPT-3 and IPT-4 domains of hepatocyte growth factor receptor, or ii) cells expressing extra-cellular domains of hepatocyte growth factor receptor, wherein said extra-cellular domains consist of the IPT-3 and IPT-4 domains, (b) measuring hepatocyte growth factor receptor activity, function and/or stability, and (c) selecting the agent that reduces hepatocyte growth factor receptor activity, function and/or stability.

2. The method according to claim 1, wherein said selected agent interferes with catalytic activity, function and/or stability of hepatocyte growth factor receptor.

3. The method according to claim 1, wherein said selected agent down-regulates catalytic activity, function and/or stability of hepatocyte growth factor receptor.

4. The method according to claim 1, wherein said selected agent is a hepatocyte growth factor receptor inhibitor and/or antagonist.

5. The method according to claim 1, wherein said selected agent is selected from the group consisting of small molecule inhibitors, aptamers, antibodies, peptides and dominant negative factors.

6. The method according to claim 1, wherein the cancer is a cancer with dysregulation of hepatocyte growth factor receptor activity.

7. A method of identifying a pharmaceutically active agent suitable for use in the treatment of cancer, comprising the steps of:

(a) putting in contact a test agent with ii) a polypeptide consisting of the extra-cellular IPT-3 and IPT-4 domains of hepatocyte growth factor receptor, or ii) cells expressing extra-cellular domains of hepatocyte growth factor receptor, wherein said extra-cellular domains consist of the IPT-3 and IPT-4 domains, and expressing the transmembrane helix and the full cytoplasmic region of hepatocyte growth factor receptor, (b) measuring hepatocyte growth factor receptor activity, function and/or stability, in the presence and absence of said test agent, and (c) selecting a test agent that reduces hepatocyte growth factor receptor activity, function and/or stability as said pharmaceutically active agent suitable for use in the treatment of cancer.

8. The method according to claim 7, wherein said measuring in step b) comprises measuring cell signalling, cell survival, and cell proliferation.

9. The method according to claim 7 wherein said polypeptide is expressed on a cell surface.

10. The method according to claim 7 wherein said polypeptide is expressed in a cell comprising a polynucleotide encoding said polypeptide.

11. The method according to claim 7 wherein said cancer is a cancer with dysregulation of hepatocyte growth factor receptor activity.

12. The method according to claim 7, wherein said active agent is selected from the group consisting of small molecule inhibitors, aptamers, antibodies, and dominant negative factors.

13. The method according to claim 7 wherein said active agent is a peptide.

* * * * *